United States Patent
Csore et al.

(10) Patent No.: US 7,363,167 B2
(45) Date of Patent: Apr. 22, 2008

(54) METHOD AND SYSTEM FOR MANAGING BLOOD PRODUCTS

(75) Inventors: Miklos Csore, Sacramento, CA (US); Gerald F. Willman, Jr., Powder Springs, GA (US); Noah L. Bentley, Folsom, CA (US)

(73) Assignee: Global Med Technologies, Inc., Lakewood, CO (US)

( * ) Notice: Subject to any disclaimer, the term of this patent is extended or adjusted under 35 U.S.C. 154(b) by 826 days.

(21) Appl. No.: 09/823,814

(22) Filed: Mar. 30, 2001

(65) Prior Publication Data

US 2002/0013523 A1 Jan. 31, 2002

Related U.S. Application Data

(60) Provisional application No. 60/193,819, filed on Mar. 31, 2000.

(51) Int. Cl.
*G06F 19/00* (2006.01)
*G06Q 50/00* (2006.01)

(52) U.S. Cl. ............................................ 702/19; 705/2
(58) Field of Classification Search ............... 702/19
See application file for complete search history.

(56) References Cited

OTHER PUBLICATIONS

Cox, C. et al. Remote electronic blood release system. Sep. 1997. Tranfusion, vol. 37, pp. 960-964.*
Brodheim (Symposium on Computers in the Clinical Laboratory, "Automated Systems in Blood Banking", in Clinics in Laboratory Medicine (1983) vol. 3, No. 1, pp. 111-132).*
Safwenberg et al. (Vox Sanguinis (1997) vol. 72, pp. 162-168).*
Butch et al. (Transfusion (1994) vol. 34, No. 2, pp. 105-109).*
Cheng (Vox Sanguinis (1998) vol. 74 (Suppl. 2), pp. 427-429).*
Kern et al. (Clinics in Laboratory Medicine (1996) vol. 16, No. 4, pp. 947-960.*
Jeter et al. (Journal of Hematotherapy (1994) vol. 3, p. 103-110).*
Coovadia et al. (Transfusion Science (1997) vol. 18, No. 4, pp. 517-522).*
Table Administration Manual (published by Wyndgate Technologies) Nov. 1999.
User's Guide (pub-lished by Wyndgate Technologies) Nov. 1999.
Reference Manual (published by Wyndgate Technologies) Nov. 1999.
Notebook containing: SafeTrace Tx Table Administration Reference Manual (published by Wyndgate Technologies) Oct. 1999 v.1.1.1.0 (cumulative to version v.1.2.0.0 filed Apr. 15, 2005).
SafeTrace Tx User's Guide (published by Wyndgate Technologies) Oct. 1999 v.1.1.1. (cumulative to version v.1.1.1.0 (cumulative to version v.1.2.0.0 filed Apr. 15, 2005).
SafeTrace Tx Reference Manual (published by Wyndgate Technologies) Oct. 1999 v.1.1.1.0 (cumulative to version v.1.1.1.0 (cumulative to version v.1.2.0.0 filed Apr. 15, 2005).

* cited by examiner

*Primary Examiner*—Lori A. Clow
(74) *Attorney, Agent, or Firm*—John E. Reilly; Ellen Reilly; The Reilly Intellectual Property Law Firm, P.C.

(57) ABSTRACT

A method and system for managing blood products and tracking their movement between a central blood test facility and a plurality of hospitals in which a database is provided for entering information pertaining to each patient, including but not limited to entering blood type information for a blood specimen from each patient, recording blood type for each blood product assigned to each patient and recording the results of remote cross-matching of each of the patient specimens and blood products to indicate their compatibility.

29 Claims, 24 Drawing Sheets

FIGURE 20

| Component Activity | | | | | | |
|---|---|---|---|---|---|---|
| Bar Code: | | | | | | |

Component Information

Product Code: 05210     RBC AS-1 IRR

Unit No: 8512301

ABO/Rh: O Pos     [N] [N] [N]

Expire Date: 02/20/2001     Time: 2359

Buttons: Close, Query, Manual, Clear

| Transaction Date/Time | Transaction | Location | Sublocation | Entered By | Entered Date/Time | Vi |
|---|---|---|---|---|---|---|
| 01/23/2001 9:58 PM | Product selection | CTS | | BVM | 01/23/2001 9:58 PM | |
| 01/23/2001 9:54 PM | Assign to available | CTS | | BVM | 01/23/2001 9:54 PM | |
| 01/23/2001 9:52 PM | Test complete | CTS | | BVM | 01/23/2001 9:52 PM | |
| 01/23/2001 9:52 PM | Component modify | CTS | | BVM | 01/23/2001 9:52 PM | |
| 01/23/2001 9:51 PM | Product selection | CTS | | BVM | 01/23/2001 9:51 PM | |
| 01/23/2001 9:49 PM | Test complete | CTS | | BVM | 01/23/2001 9:49 PM | |
| 01/23/2001 9:47 PM | Received | CTS | | BVM | 01/23/2001 9:47 PM | Y |

FIGURE 22

METHOD AND SYSTEM FOR MANAGING BLOOD PRODUCTS

REFERENCE TO APPENDED ITEMS

This application claims the benefit of Provisional Ser. No. 60/193,819, filed 31 Mar. 2000 for METHOD AND SYSTEM FOR MANAGING BLOOD PRODUCTS, by Miklos Csore et al and owned by the assignee of the present application.

Reference is also made to SafeTrace Tx Table Administration Manual, Release v1.2.0.0 published November, 1999, SafeTrace Tx User's Guide, published November, 1999, and SafeTrace Tx Reference Manual, also published November, 1999, all published by Wyndgate Technologies of El Dorado Hills, Calif., said publications incorporated by reference herein.

BACKGROUND AND FIELD

The following relates to blood product management and more particularly relates to a novel and improved computer programmable method and system for blood product management including cross-matching and compatibility testing of blood products as well as the ability to display information about a patient during the preparation of blood components prior to transfusion and which is specifically adaptable for use in hospitals, clinics and the like.

There is a long-felt need for a blood product management system to help prevent the release of unsafe, unsuitable or ineffective blood products to patients. In a hospital, when an order comes down from a given floor or section of the hospital requesting blood, it is communicated to the blood bank which is typically located at the hospital. The blood bank will search for a suitable product for the patient, i.e. a suitable red blood cell, and in many situations must cross-match the blood product requested with the blood of the patient. Once successfully cross-matched, the blood product is then selected and made ready for issue. Another order or request will then be transmitted when the blood product is actually needed at which time the cross-matched product is delivered to the responsible personnel for providing a blood transfusion for the patient.

It is important to control the compatibility of a blood component and patient's blood to ensure safe transfusion of the component to the patient. This requires tracking of the patient blood attributes and blood component attributes by their respective antigens and antibodies. In addition, it is desirable to incorporate a patient information toolbar into the computer program for displaying and controlling critical patient information during the preparation of blood products prior to transfusion. This information includes patient special needs, patient comments, patient transfusion reactions, availability of autologous blood components, availability of directed blood components, significant antibodies, patient blood type, expiration of the current patient specimen, and reserved blood components.

The following definitions are given to assist in better understanding the system and steps followed in carrying out the present invention:

"Antigen": A substance that induces the formation of antibodies and assists the body to distinguish between itself and a foreign substance.

"Antibody": A protein produced by the immune system in response to the presence of an antigen.

"Blood Type" A blood type is a way to classify blood into various groups. A blood type is determined by the presence or absence of antigens on the red blood cells, and the presence or absence of antibodies in the serum. A blood type definition in the computer database is the combination of antibodies and antigens for each blood group (ABa/Rh)

"Blood Component": A blood component, also referred to as "blood product", is one of the portions of a unit of whole blood. Whole blood contains red blood cells, white blood cells and platelets suspended in a watery fluid called plasma. Blood components include red blood cells, plasma, platelets and cryoprecipitated antihemophilic factor (AHF).

"Significant Antibodies": Any antibody, other than those for A and B (which are expected), that might cause a serious ("hemolytic") reaction after transfusion of blood containing the corresponding antigen.

"Segment": A portion of the blood component that can be detached and subsequently used for testing.

"Product ID Tag": The Product ID Tag is attached to the blood product being processed or issued to a patient. It contains information about the patient and the blood product to help in the identification and validation of the patient and product. The Product ID Tag is one of the mechanisms that transfusion services and hospitals use to verify that the patient and the product are correctly matched before transfusion. A typical Product ID Tag consists of three different sections:

1. Patient Information Section. This section contains critical patient information necessary to identify the patient. It is used to identify the patient in regard to the hospital, blood type and blood antibodies, as well as special needs associated with the patient.

2. Product Information Section. This section contains relevant product specific information regarding unit of blood to which this section is physically attached. This section is used to identify the unit of blood, blood type, and antigens. In addition to the product information, it contains information regarding cross-match testing, and lists any prohibiting factors and comments relevant to issuing of this product to the patient identified in the Patient Section of the report.

3. Transfusion Information Section. This section is created for recording handwritten information during transfusion. This section is a form that is filled out by the technician before, during and after transfusion of the product attached to the report. This section is used to record relevant information to the transfusion process, which can later be entered into the computer program database.

Accordingly, there are specific requisites to reliable, secure cross-matching of certain blood products, namely, receiving an order for the blood product, tracking segments of the blood components in inventory, locating a specimen of the patient's blood and transferring it to a given location, which typically would be a lab or blood bank at the hospital where the inventoried blood segments are located.

It is therefore a feature to control the remote testing of compatibility of a blood product and patient specimen to ensure the safety of the blood component transfusion into the human body by using a segment of the blood product assigned at the lab and mixing it with a portion of the patient specimen so as to achieve efficiency in the delivery of blood components both for emergency and non-emergency situations.

Another feature is to provide a computer system that enables remote testing of patient blood and a segment of the blood component intended for transfusion remotely through the steps of (a) assigning a blood product, which is typically stored at a central facility, to a patient for testing at the central facility and preparing a segment of the blood component; (b) transferring to the facility a blood specimen drawn from the patient; (c) testing the segment of the blood component assigned with the blood specimen drawn from the patient to determine their compatibility; (d) whether or not compatible, printing a product ID tag at the facility where the blood component is located; and (e) continuously tracking movement of the blood product and specimen between the central facility and hospital on a database.

Another feature is to track patient blood attributes and blood component attributes in such a way as to ensure that the attributes are compatible with each other as well as to ensure that the transfused blood component is compatible with the patient who is receiving the transfusion.

A further feature is to provide for a novel and improved method and means for displaying critical patient information during the preparation of blood products prior to transfusion so as to make readily available to the medical technician important current and historical information about the patient.

In one aspect, a method of managing and tracking blood products is provided for use between a plurality of remote patient facilities and a central blood testing facility including the steps of obtaining a blood specimen from each patient who requires a blood reserve, selecting a blood product for cross-matching with each said patient specimen, cross-matching each said patient specimen and said blood product to determine their compatibility with one another, and providing a database for the entry of information pertaining to each patient. Preferably, the step of storing information is further characterized by information relating to a patient's special needs, prior transfusion history, autologous blood availability and its location, blood type and patient specimen expiration date. Still further, the method is characterized by being able to record information as to the location and patient blood attributes in the database.

A system has been devised for managing and tracking blood products between a central blood test facility and a plurality of remote facilities which includes means for recording information on a database which identifies each patient requiring a blood reserve, means for obtaining a blood specimen from each said patient, means for assigning a segment of a blood product for cross-matching and for cross-matching each said segment and patient specimen to determine their compatibility with one another, and means for identifying each segment and patient specimen determined to be compatible as well as storing same in the computer.

The above and other objects, advantages and features will become more readily appreciated and understood from a consideration of the following detailed description of preferred and modified forms when taken together with the accompanying drawings in which:

BRIEF DESCRIPTION OF THE DRAWINGS

FIG. 20 is a screen display of patient information;

FIG. 22 is a screen display of information stored in tracking the location of blood components.

DETAILED DESCRIPTION OF ONE EMBODIMENT

The one embodiment herein described allows a blood bank to maximize its efficiency in cross-matching a blood component to a patient for transfusion. This efficiency will result in improved patient care by the blood bank and the hospital. This process allows timesaving during the testing and the time needed to transfer the blood product to the patient site. The requirements for this process are to have complete tracking of the blood component, the blood component segment, the patient, and the patient specimen. Any one of these requirements not met could result in a mismatch of the component and the patient which can result in serious health problems to the recipient of the blood.

Figure 1:
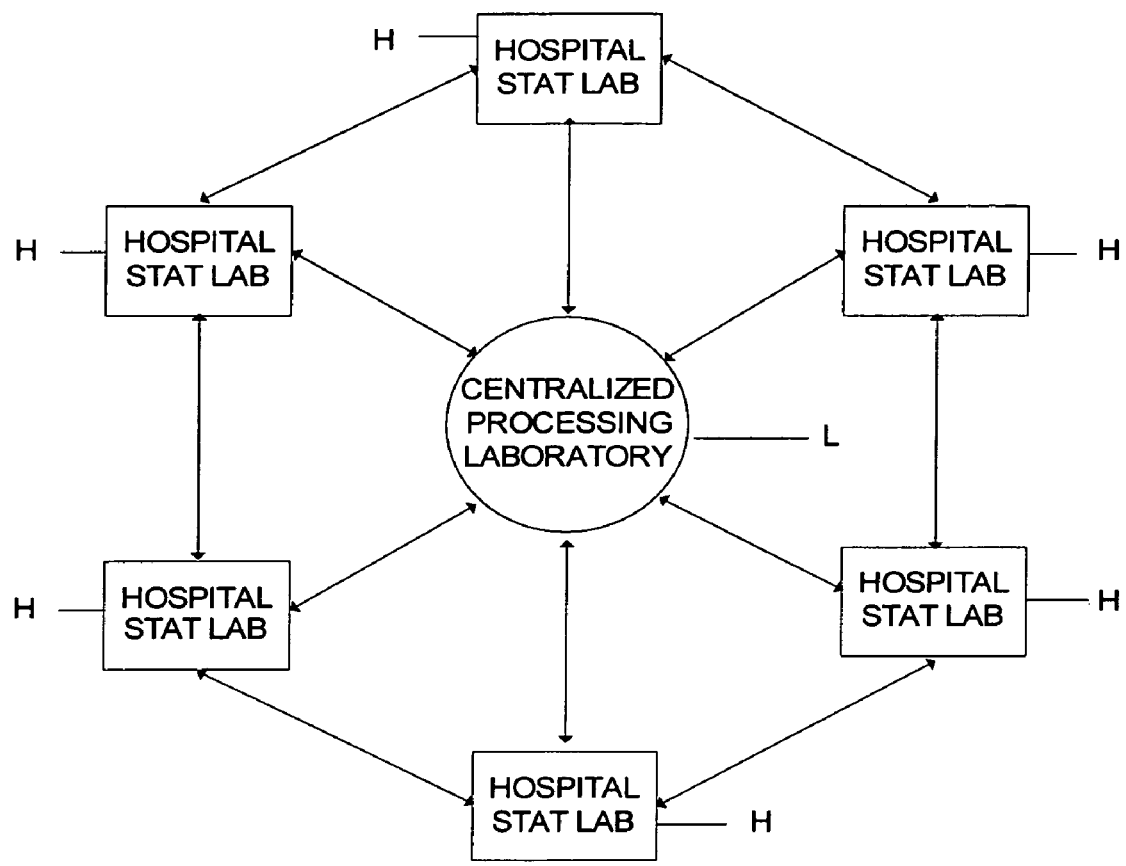
FIG. 1 is a flow diagram of a centralized transfusion model with multiple hospitals.

The remote cross-match capability allows a group of hospitals to be organized to include a common or centralized facility or transfusion service to share a common laboratory to perform blood testing as well as cross-match work for all hospitals in the group. This reduces the amount of staff required at the hospitals. Typically, each hospital will have only a stat laboratory to handle its emergency patient/product cross-match needs. FIG. 1 depicts a typical centralized or common transfusion model L having a "centralized processing laboratory 1" with multiple hospitals H.

The hospital is able to track the location of the patient specimen, segment of the blood component and the blood component itself. The cross-match compatibility testing is completed using the segment of the blood component and the patient specimen while the blood component resides at a different location. This process will allow efficient and timely delivery of blood components in both emergency and non-emergency situations.

Figure 2:
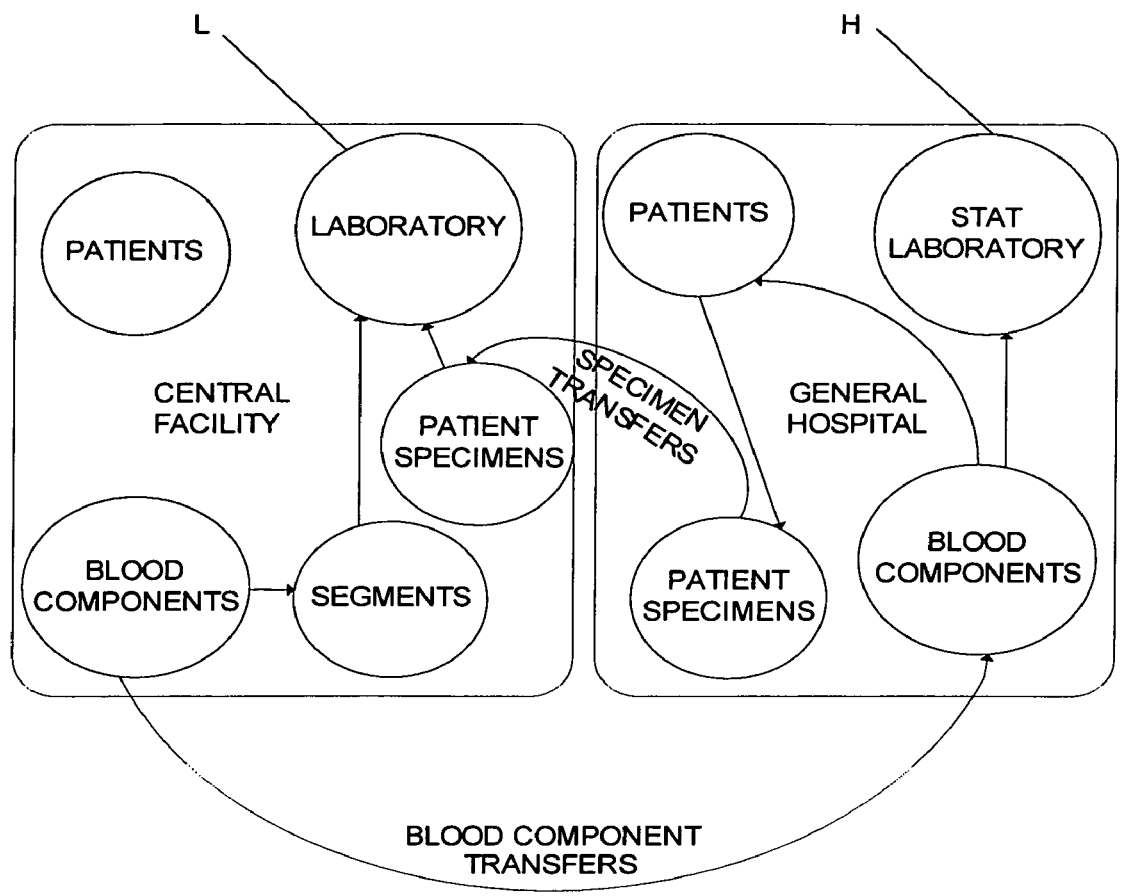
FIG. 2 is a flow diagram of a central facility and one of the hospitals illustrated in FIG. 1 which illustrates the location of inventory, segments, patient specimens and patients.

Before a remote cross-match can be performed, the following conditions must exist: (a) the patient exists in the system with current visit information, (b) the patient has a current blood specimen and the specimen has been transferred to the central facility, (c) the patient has an order for a blood component and a cross-match test, (d) the blood component has an available segment, and (e) the blood component that will fill the order resides at the hospital where the patient is located and a segment of that blood component is at the central facility with laboratory L. FIG. 2 depicts a central facility including the laboratory L and one of the hospitals H and where the inventory, segments, patient specimens and patients are located.

Completing the remote cross-match is the process wherein a lab technician at the central laboratory L assigns a blood component identified by a segment to a patient specimen. Once the assignment is made, the lab technician proceeds to test the segment with the patient specimen to determine compatibility. Upon completing the cross-match test, the lab technician enters the results into the computer program database. Once the results are saved, the product ID tag will be printed at the location L of the blood component and the blood component will be ready to issue to the patient.

Figure 3:
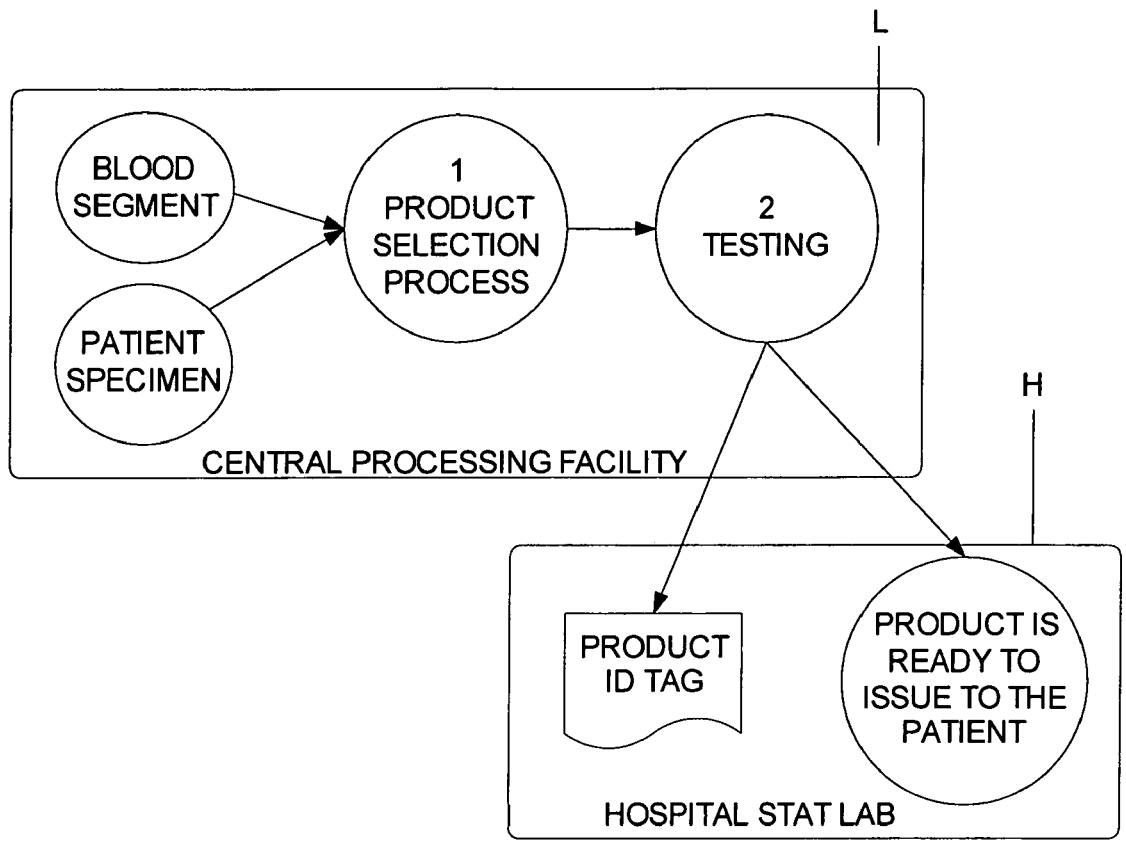
FIG. 3 is a flow diagram illustrating completion of remote cross-match testing.
Figure 18:
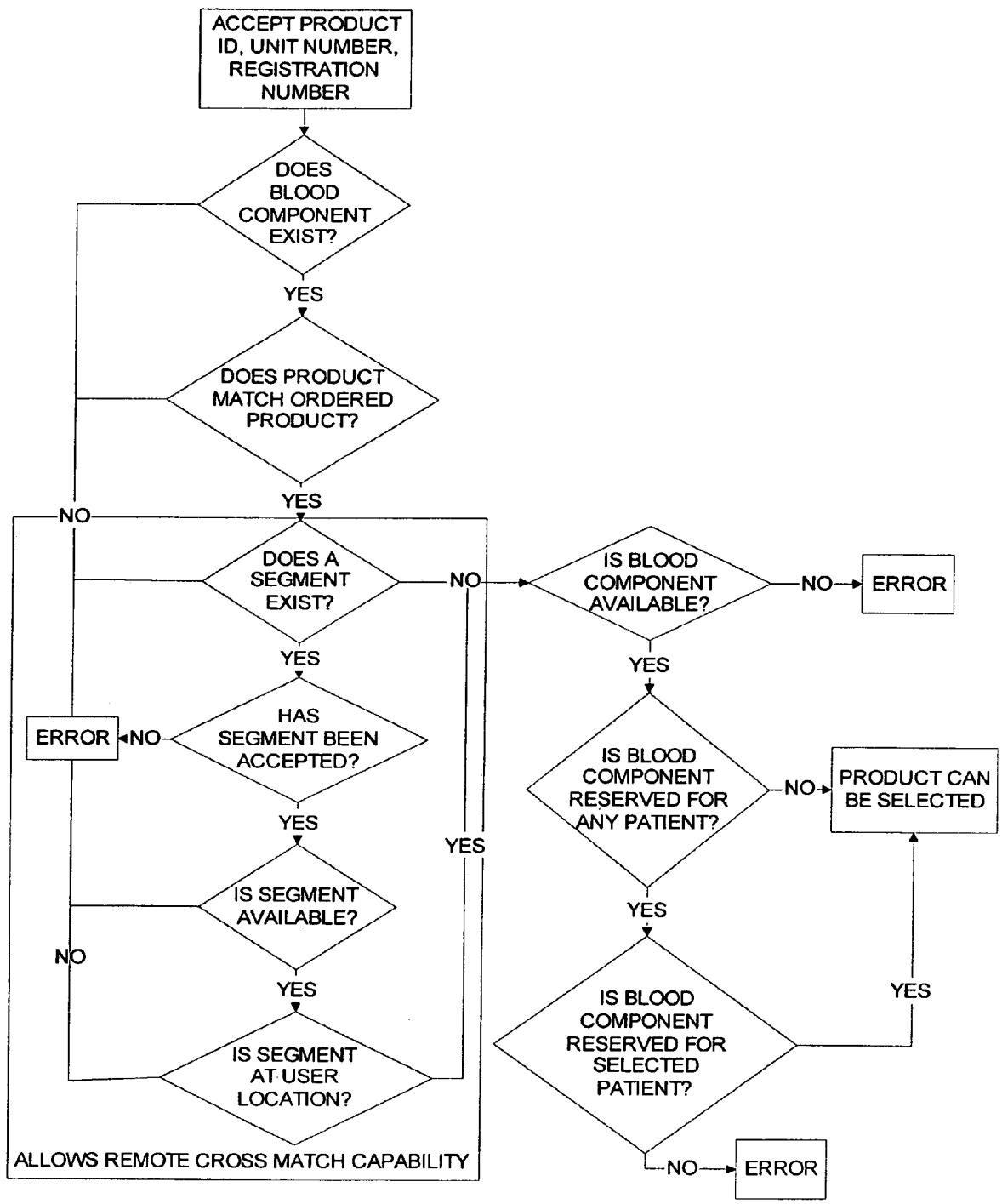
FIG. 18 is a flow chart showing product selection steps followed in remote cross-match testing.
Figure 19:
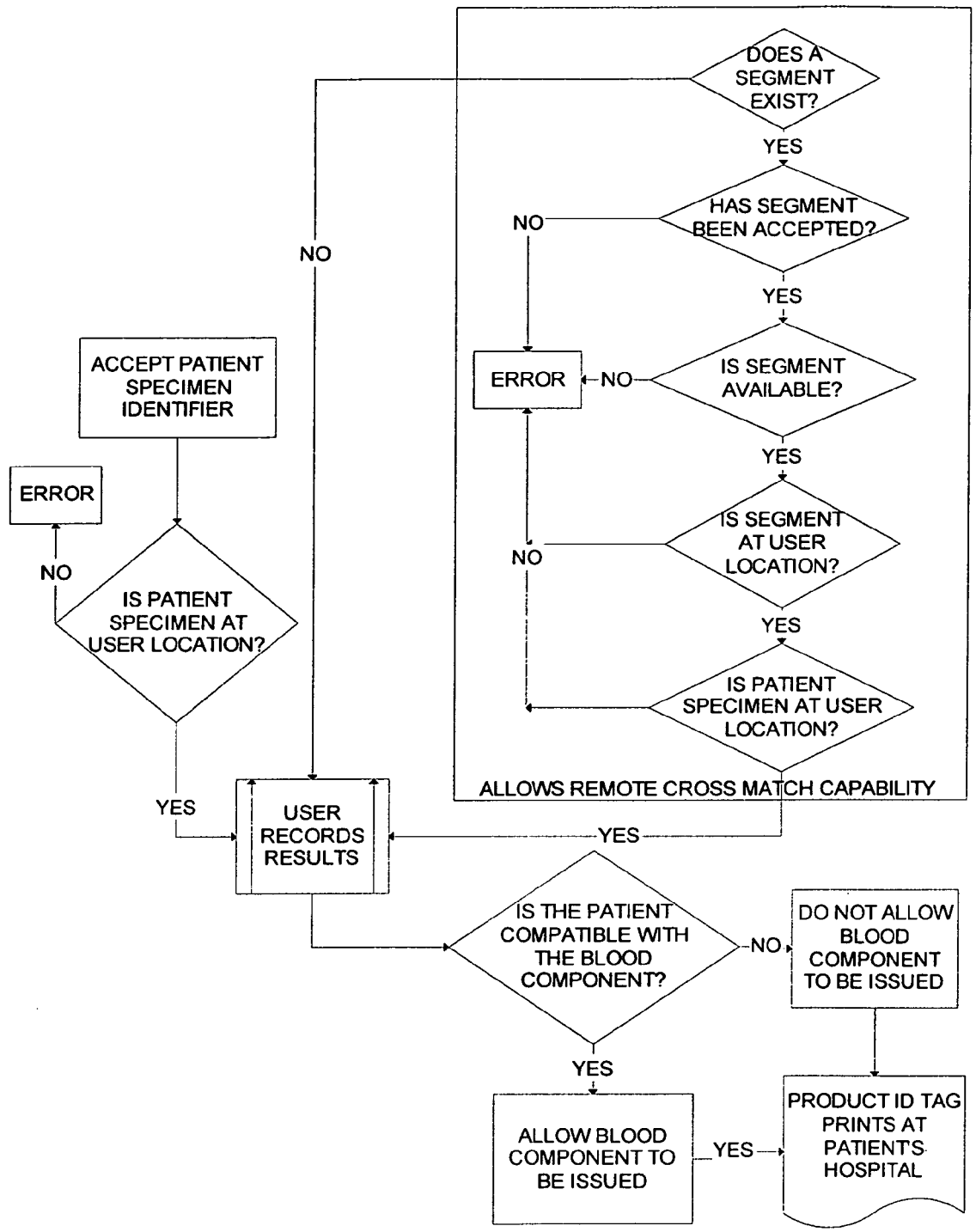
FIG. 19 is a flow chart illustrating test result entry steps related to remote cross-match functionality.

As shown in FIG. 3, the laboratory technician at the central facility assigns a blood component identified by the segment to the patient. During this product selection process, as shown in FIG. 18, the computer program runs the following checks: (a) verifies that the product ID of the entered component matches the selected order item; (b) if the entered component has an active segment, then the segment must be entered by clicking the segment command button; (c) verifies the location and status of the segment (the segment must be available and located at the facility making the selection); (d) verifies the state of the component; and (e) if the entered component is reserved, make sure that the component is reserved for the designated patient. In testing, the laboratory technician performs the cross-match test at the work bench. Upon completion of the serological testing, the technician enters the results into the computer program database. The computer program database forces the technician to verify the patient specimen identifier and the blood component segment identifier before allowing them to record the results of the test. During the result entry process, as shown in FIG. 19, the computer program runs the following checks: (a) verifies that the specimen is at the user's location for abbreviated or unabbreviated cross-match test and (b) verifies that the segments are at the user's location for abbreviated or unabbreviated cross-match test.

When the technician has completed the data entry of the test results, the results are written to the database. For each completed cross-match test, a product ID tag is printed at the facility where the blood component is located. Any blood components associated with cross-match tests that were compatible will be available for issue at the location of the patient and blood component.

Figure 4A:
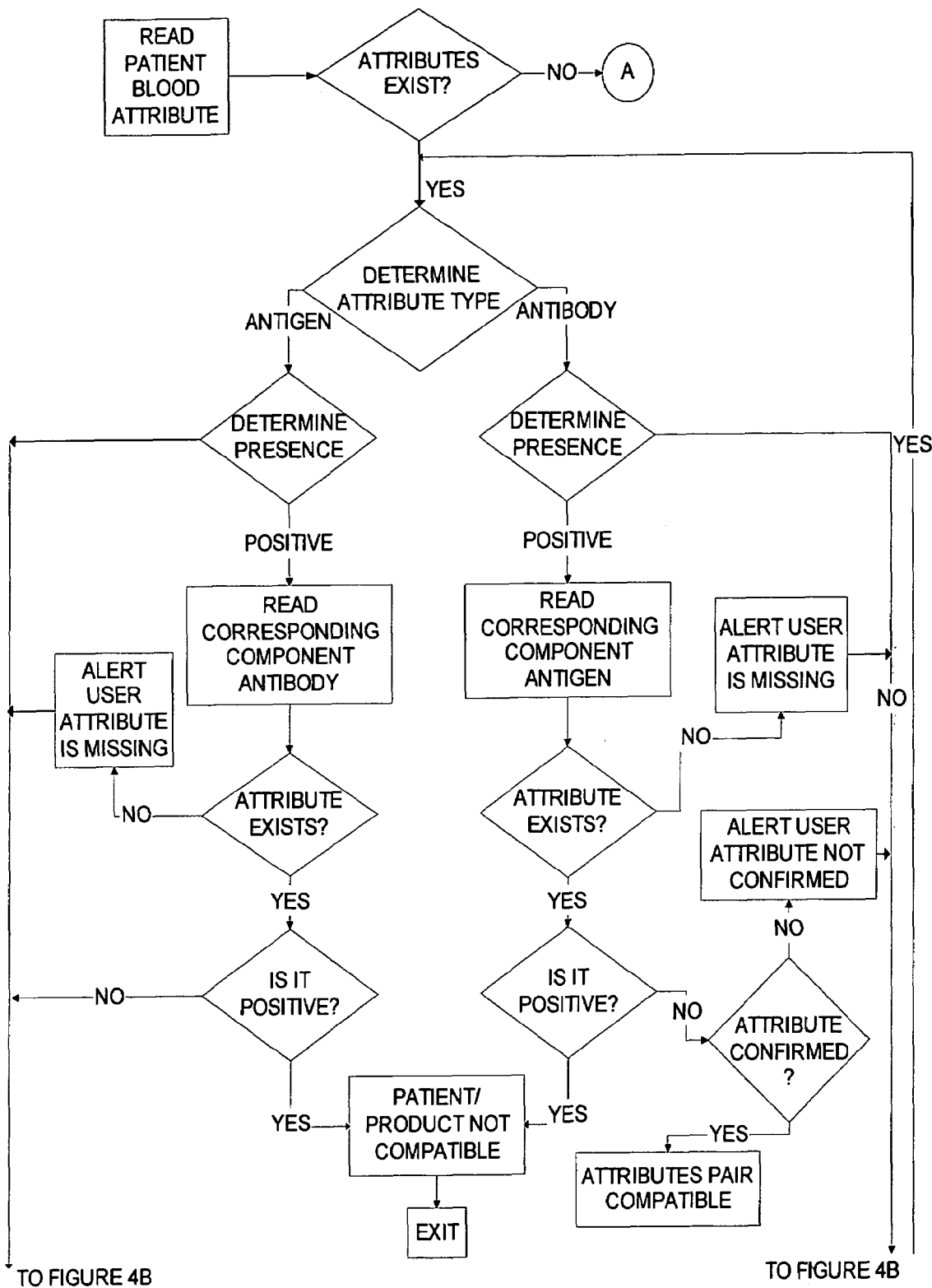
FIGS. 4A and 4B is a flow chart illustrating the logic used in a standard compatibility test.
Figure 4B:
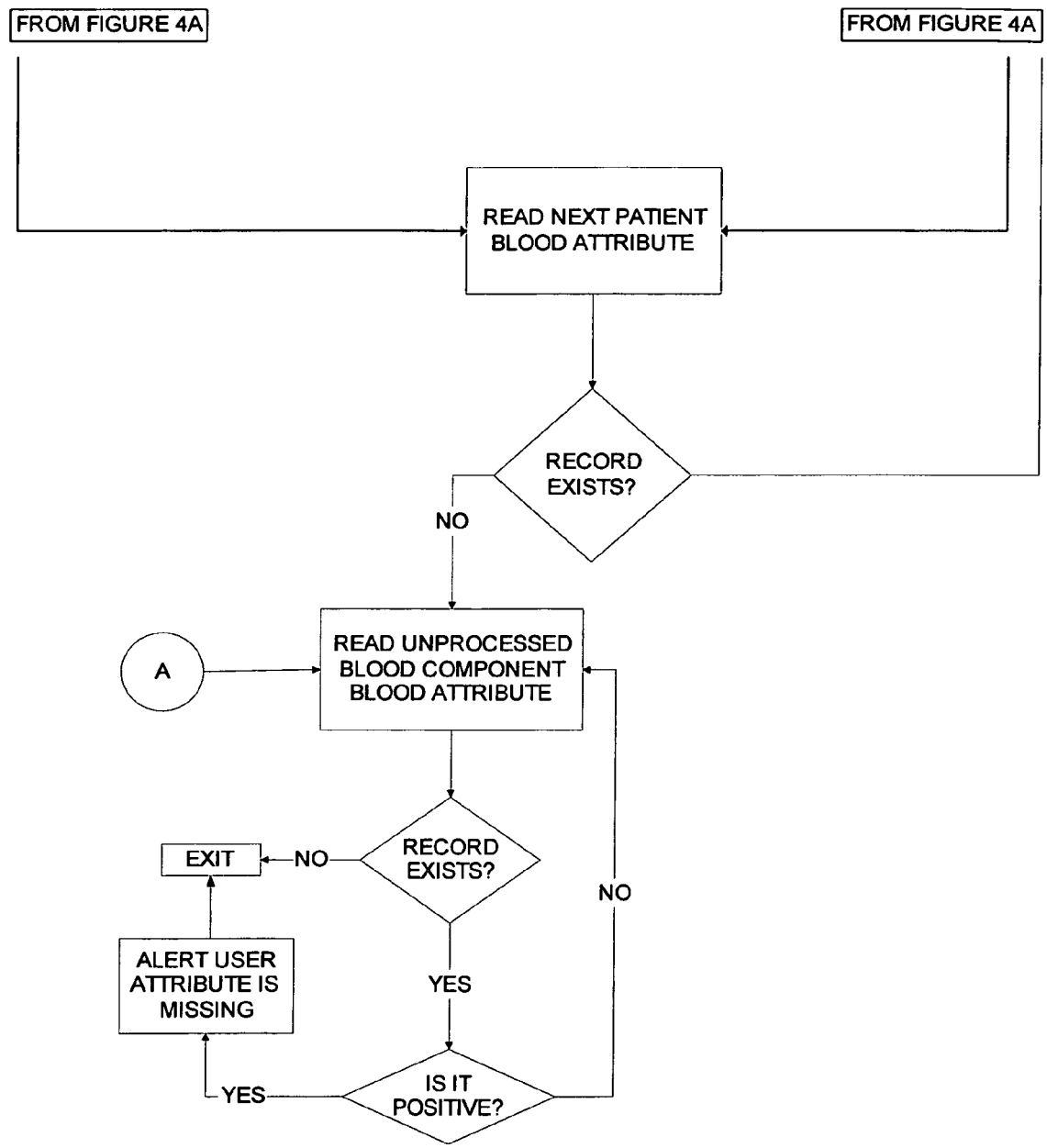

Patient/product compatibility is carried out by determining the patient blood attributes and the blood component attributes by their respective antigens and antibodies. As shown in FIGS. 4A and 4B, standard compatibility compares the patient's antigens with the blood component's corresponding antibodies and blood component's antigens with the patient's corresponding antibodies. When comparing the corresponding antigen and antibody pairs, the incompatibility is determined by a positive presence in both the antigen and antibody. Further, the blood component antigen or antibody may require confirmation by the blood bank for the compatibility comparison to be successful. As illustrated in FIGS. 4A and 4B, when this situation occurs, the user is alerted that a blood component's blood attribute has not been confirmed by the blood bank. If one-half of the pair is missing either from the patient or the blood component, the user is alerted that a blood attribute is missing; further testing on the patient's blood or the blood component is required to determine compatibility.

The following Table illustrates a sample compatibility test between the patient and the blood component:

TABLE I

| Patient Antibody | Component Antigen | Component Attribute Confirmed | Compatible |
|---|---|---|---|
| K Positive | K Positive | N/A | No |
| K Positive | K Negative | Yes | Yes |
| K Positive | K Negative | No | Unknown |
| K Positive | K Unknown | N/A | Unknown |

FIGS. 4A and 4B illustrates the logic employed in carrying out standard compatibility tests.

Auto-compatibility compares the antigens and antibodies within either the patient or within the blood component. The new or updated antigen is compared with the corresponding antibody or the new or updated antibody is compared with the corresponding antigen. If both the antigen and antibody have a positive presence, then the patient or blood component is incompatible with itself. When this situation occurs, the computer program database alerts the user that the new or updated blood attribute is not compatible with the existing blood attribute information. These checks help reduce data entry errors.

Figure 5:
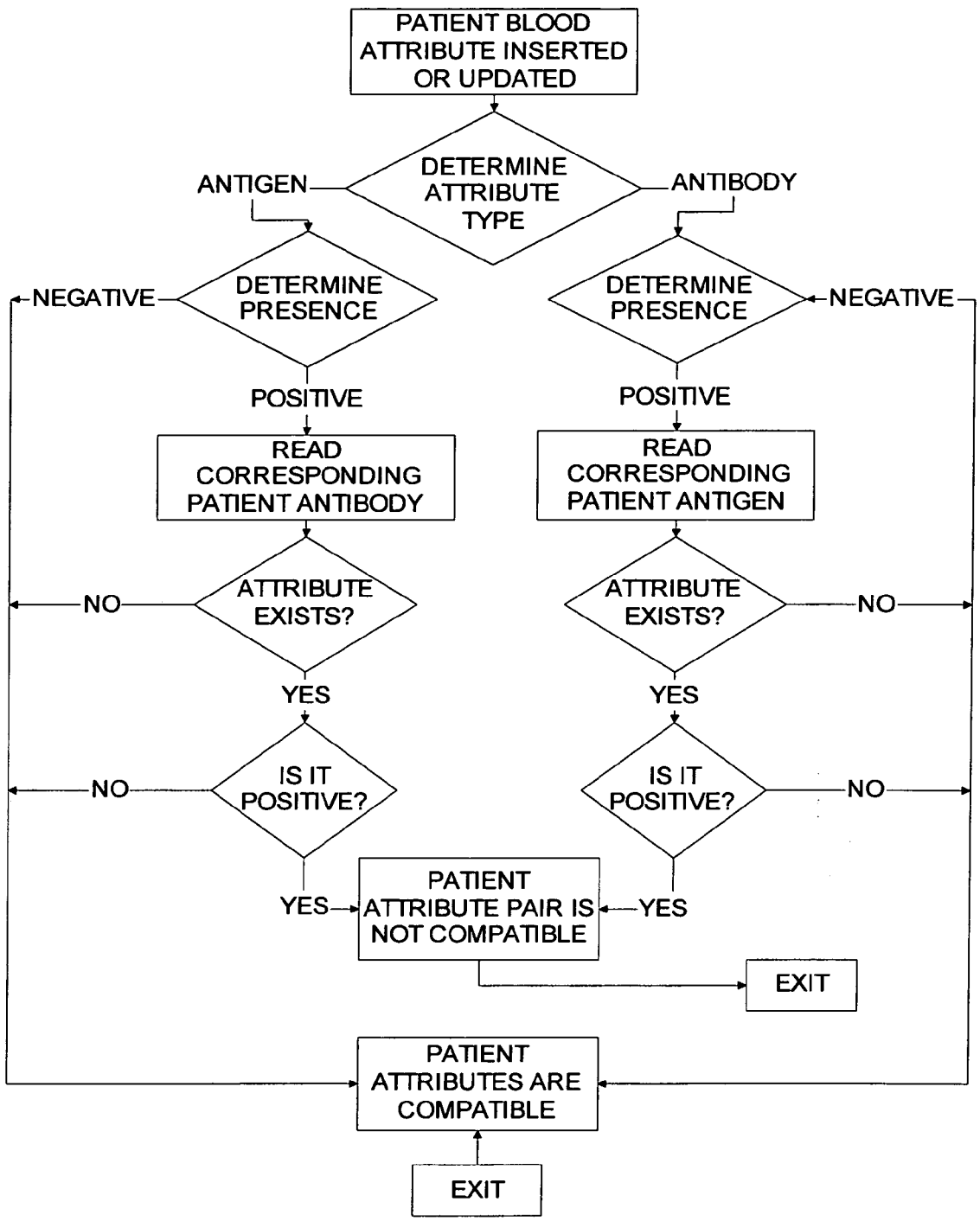
FIG. 5 is a flow chart illustrating the logic used in a patient auto-compatibility test.
Figure 6:
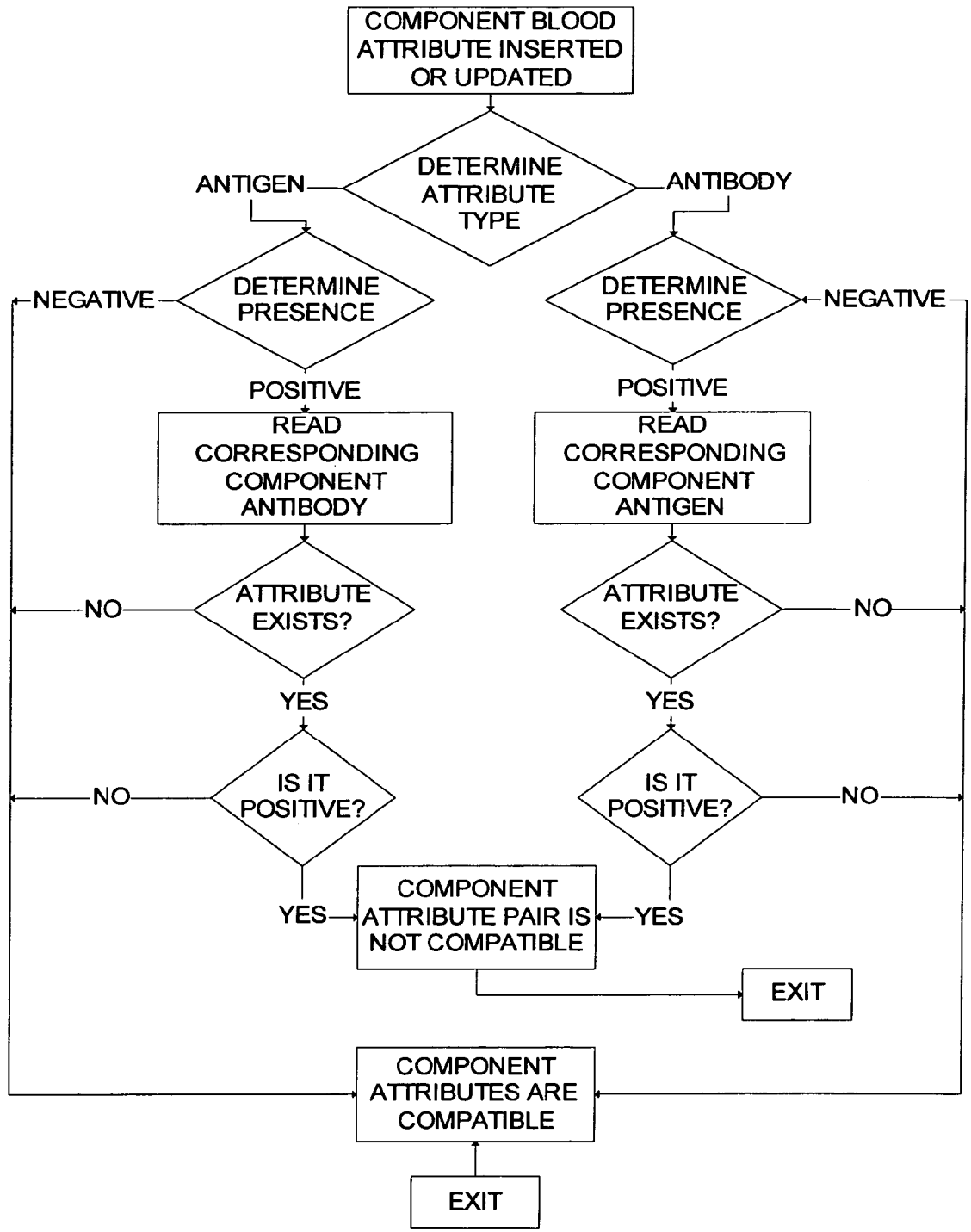
FIG. 6 is a flow chart illustrating the logic used in a product auto-compatibility test.

FIG. 5 illustrates the logic used in testing patient auto-compatibility, and FIG. 6 illustrates the logic used in testing blood component auto-compatibility.

Figure 7A:
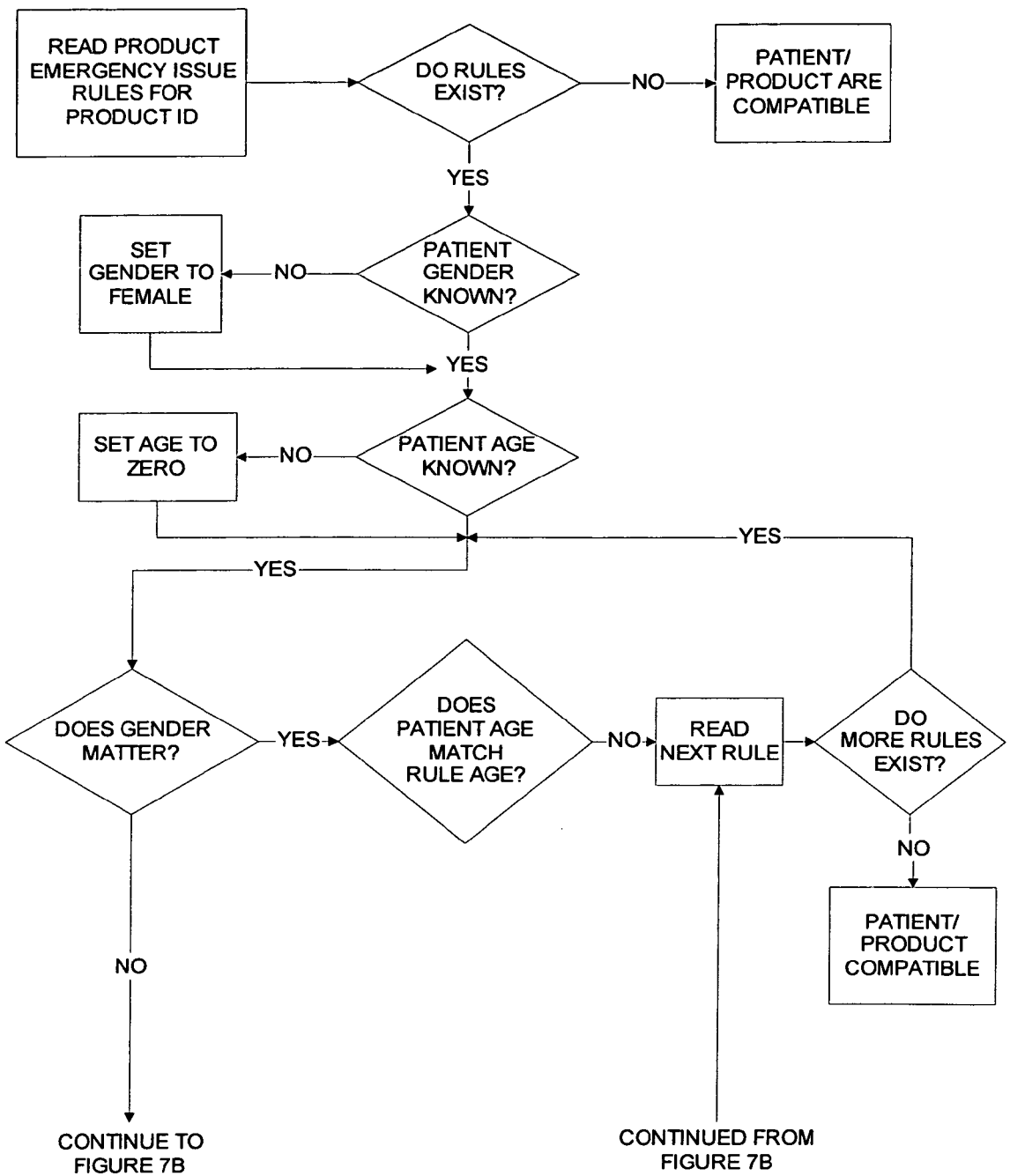
FIGS. 7A and 7B is a flow chart illustrating the logic used in an emergency patient product compatibility test.
Figure 7B:
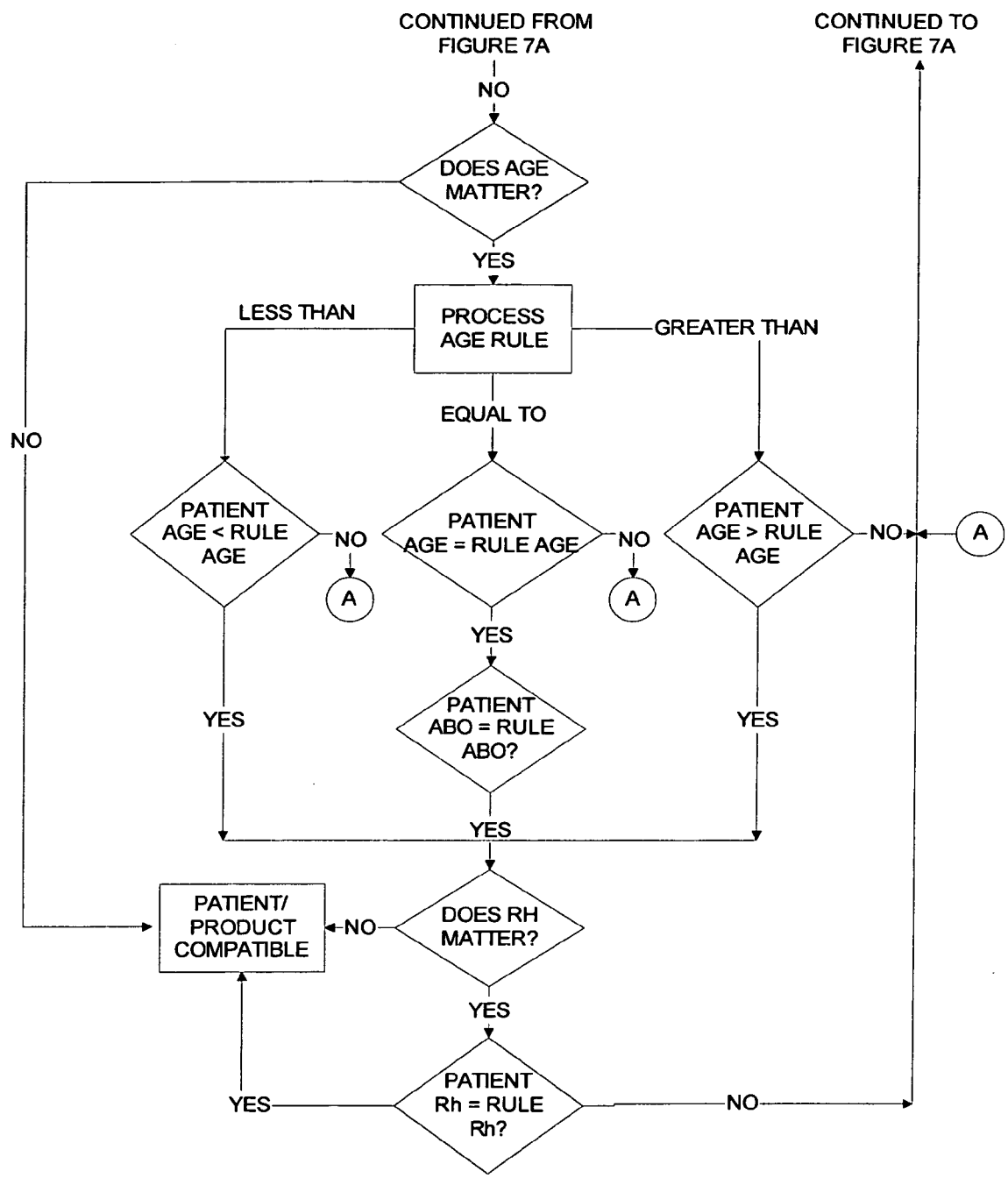

When the patient is unknown to the computer system or the patient is known but there is no current specimen and/or no blood type test on the current specimen, as illustrated in FIGS. 7A and 7B, an emergency compatibility check is run to determine if the blood component selected can be issued to the patient. The emergency issue results are controlled by the users to fit the industry defined standards for a given product ID. The following Table illustrates a sample of the rules that may be used by a blood bank:

TABLE II

| Product ID | Age Operator | Age | Gender | ABO | RH |
|---|---|---|---|---|---|
| RBC | Greater than | 50 | Female | 0 | |
| RBC | Less Than | 50 | Female | 0 | Neg |
| RBC | | | Male | 0 | |
| FFP | | | | AB | |
| Gran | Greater than | 50 | Female | 0 | |
| Gran | Less Than | 50 | Female | 0 | Neg |
| Gran | | | Male | 0 | |

Figure 8:
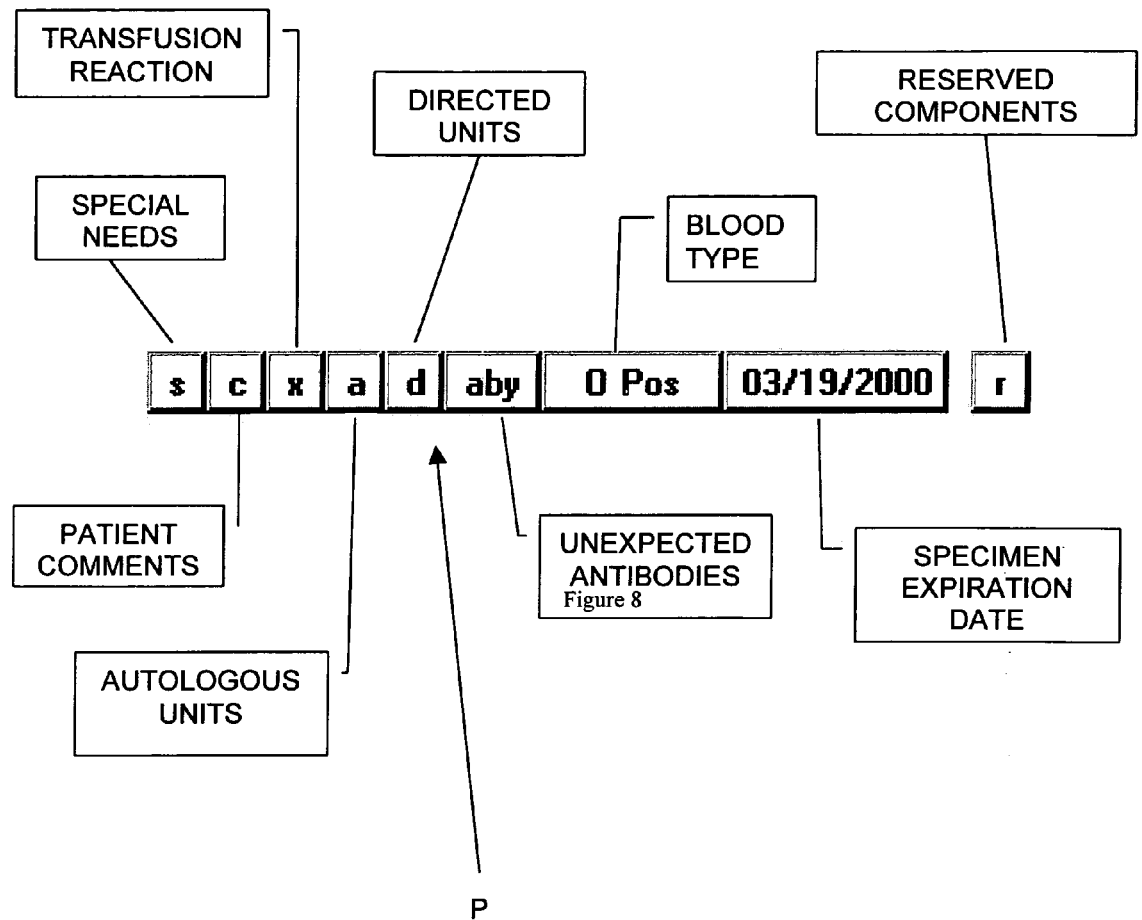
FIG. 8 is a screen display of a patient bar.
Figure 20:
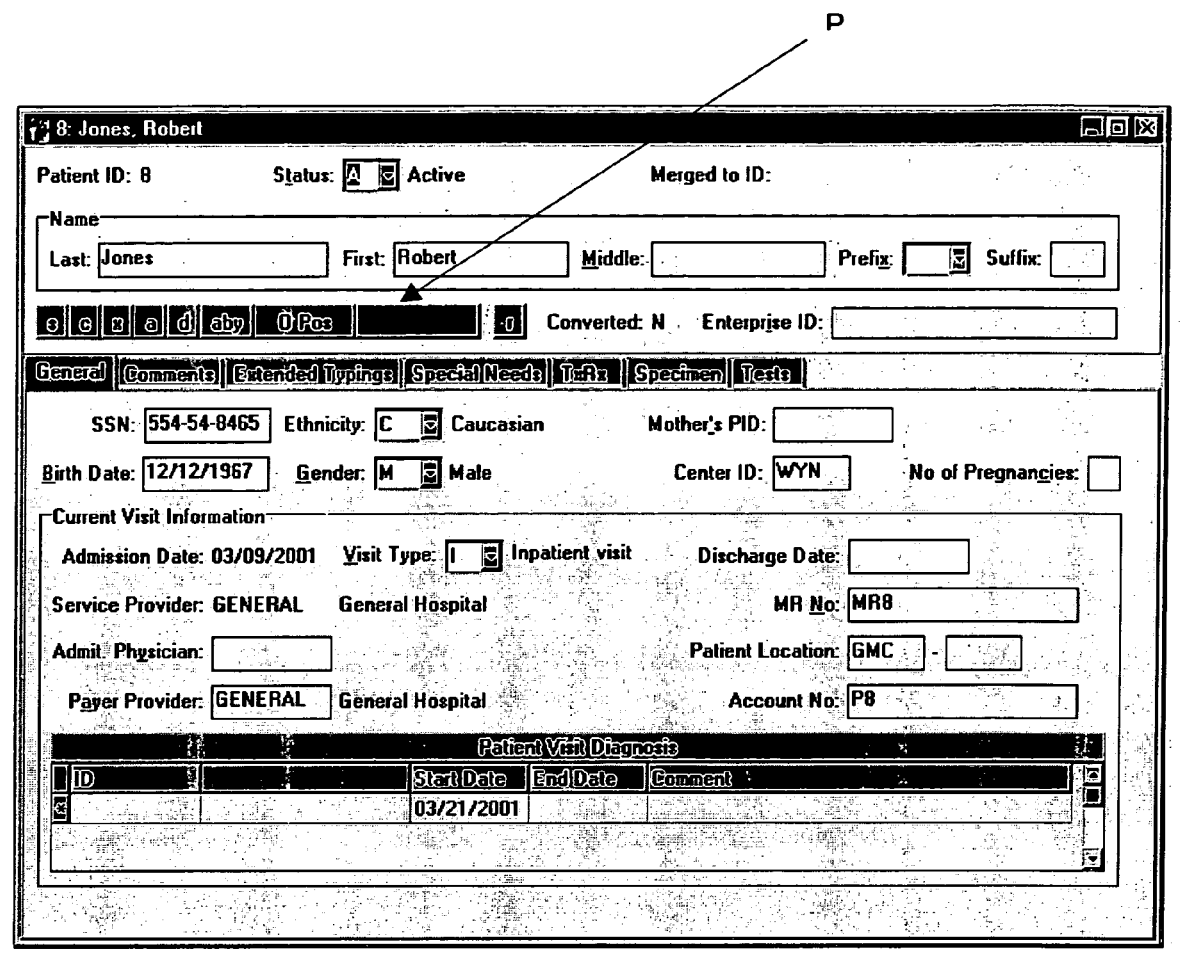

There is illustrated in FIG. 8 a patient bar P which affords access to information stored in the computer pertaining to each patient and blood products for that patient in response to passing in a patient identification number used to uniquely identify a patient in the database. FIG. 20 illustrates a typical patient profile screen which displays the patient bar P in conjunction with a particular patient having a patient identification number as displayed at "Patient ID".

Button captions of the patient bar P are driven by the current state of patient information which is drawn from the database.

Specifically, the button s provides a visual indication that the patient has special needs. If the button displays as a capital "S", then there are active special needs for the patient; otherwise, a lower case "s" means no current special needs exist, as illustrated in FIG. 8. Clicking the button s accesses the patient's special needs information stored in the computer on a patient profile form. Patient special needs information is defined by the client and normally includes clinical information about the patient that constrains the scope of blood products which are appropriate for use by a particular patient. These needs are most often critical safety indicators which must be considered when selecting blood products for patient transfusion. Failure to consider patient special needs when selecting and testing blood products can be considered as a serious safety issue.

Figure 9:
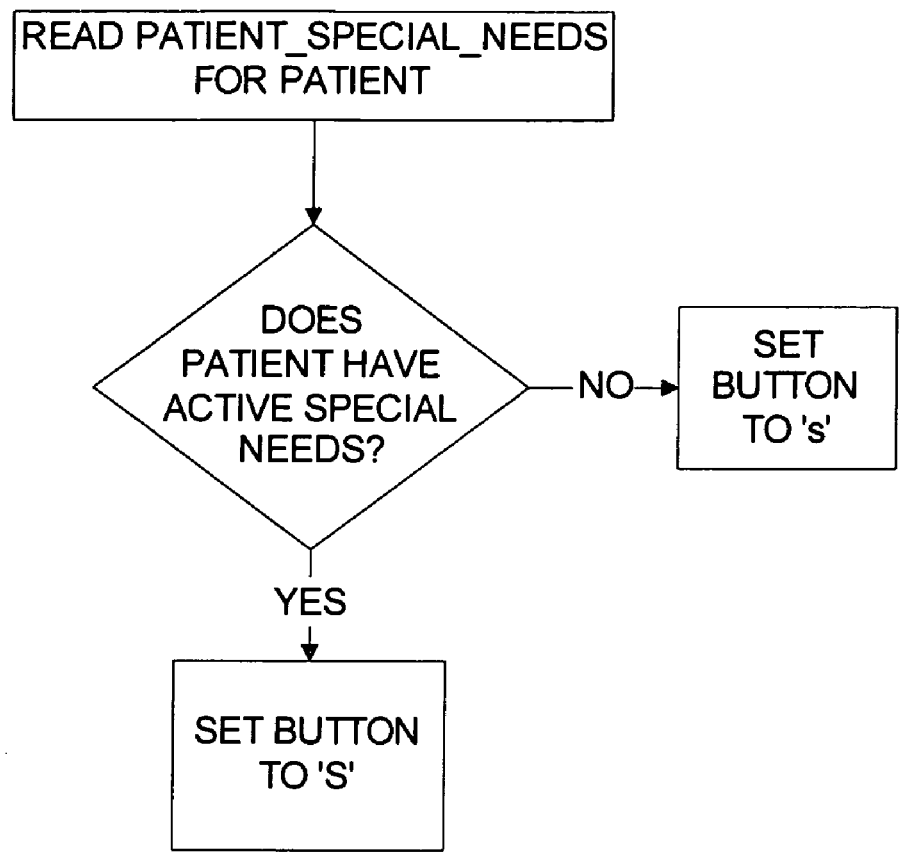
FIG. 9 is a flow chart illustrating the logic used in button s of the patient bar.

A patient "comments" button c provides a visual indication of patient comments. Again, if the button c displays as a capital "C", then there are active comments; otherwise, a lower case "c" means no current comments exist, as illustrated in FIG. 9. Clicking the button C accesses any patient comments as stored in the computer.

Patient transfusion reaction information is used to document clinical information about the patient when the patient has had a reaction to a prior transfusion. This type of reaction is often followed up by subsequent post-transfusion testing to help determine the possible causes of the reactions. A reaction history may constrain the scope of blood products which are appropriate for use by a particular patient. Failure to consider prior transfusion reaction information when selecting and testing blood products may be considered a serious issue.

Figure 10:
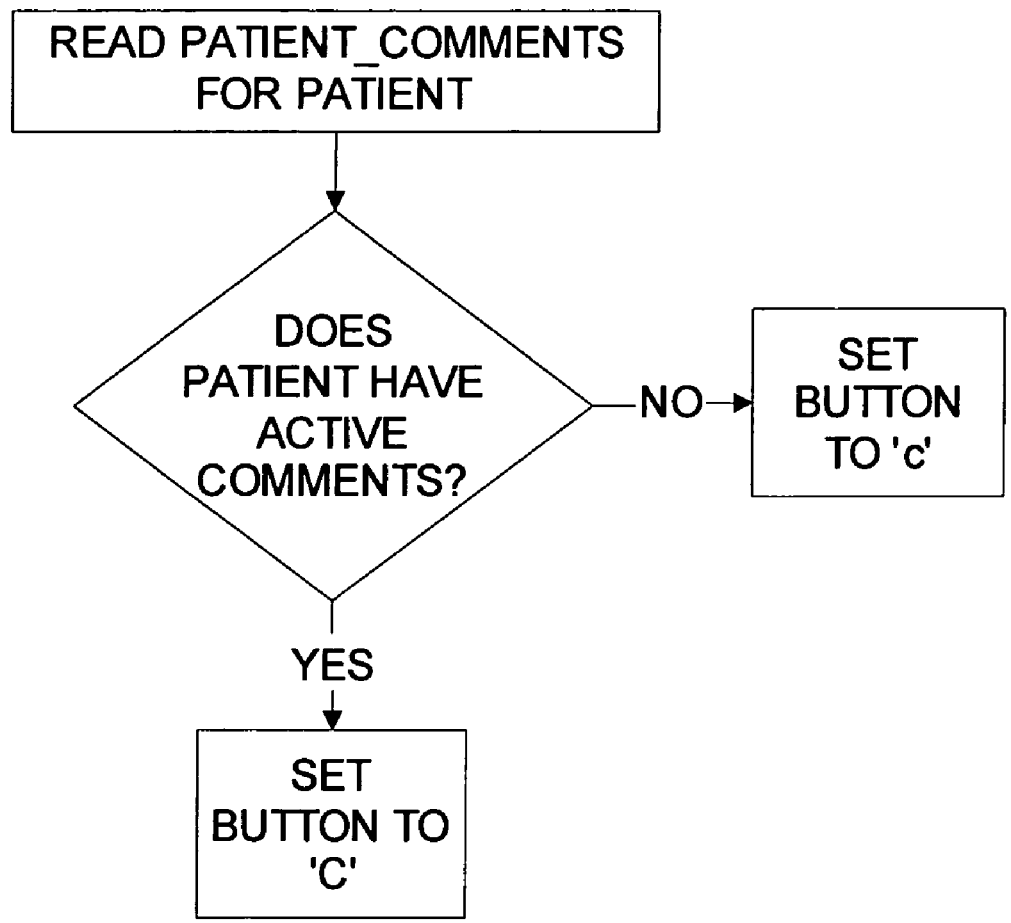
FIG. 10 is a flow chart illustrating the logic used in button c of the patient bar.

The button x provides a visual indication of transfusion reaction information of a patient. Thus, an upper case "X" indicates that the patient has had a transfusion reaction; otherwise, a lower case "x" means no transfusion reaction has been recorded in the system as illustrated in FIG. 10. Clicking the button X accesses any transfusion reaction information stored in the computer.

Figure 11:
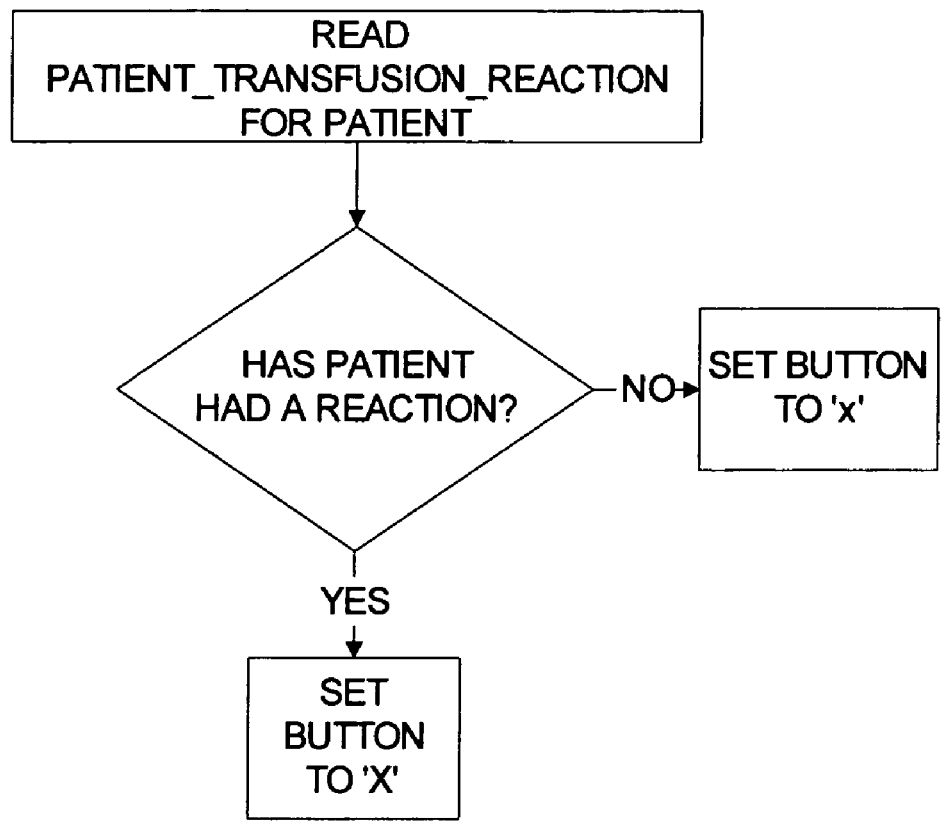
FIG. 11 is a flow chart of the logic used in connection with the button x of the patient bar.

The button a provides a visual indication of the availability of at least one unit that is identified as an autologous donation for the patient which has not expired, not transfused, not shipped, not discarded, not consumed or crossed-over. If the button displays a capital or uppercase "A", there is at least one such donation in inventory; otherwise, a lower case "a" means "none", as illustrated in FIG. 11.

Autologous components are blood products (i.e. whole blood) which the patient has donated specifically for his or her personal use. A patient who is scheduled for surgery where a transfusion may be required will often donate blood prior to surgery. This blood is categorized as autologous and is the preferred choice for transfusion.

Figure 12:
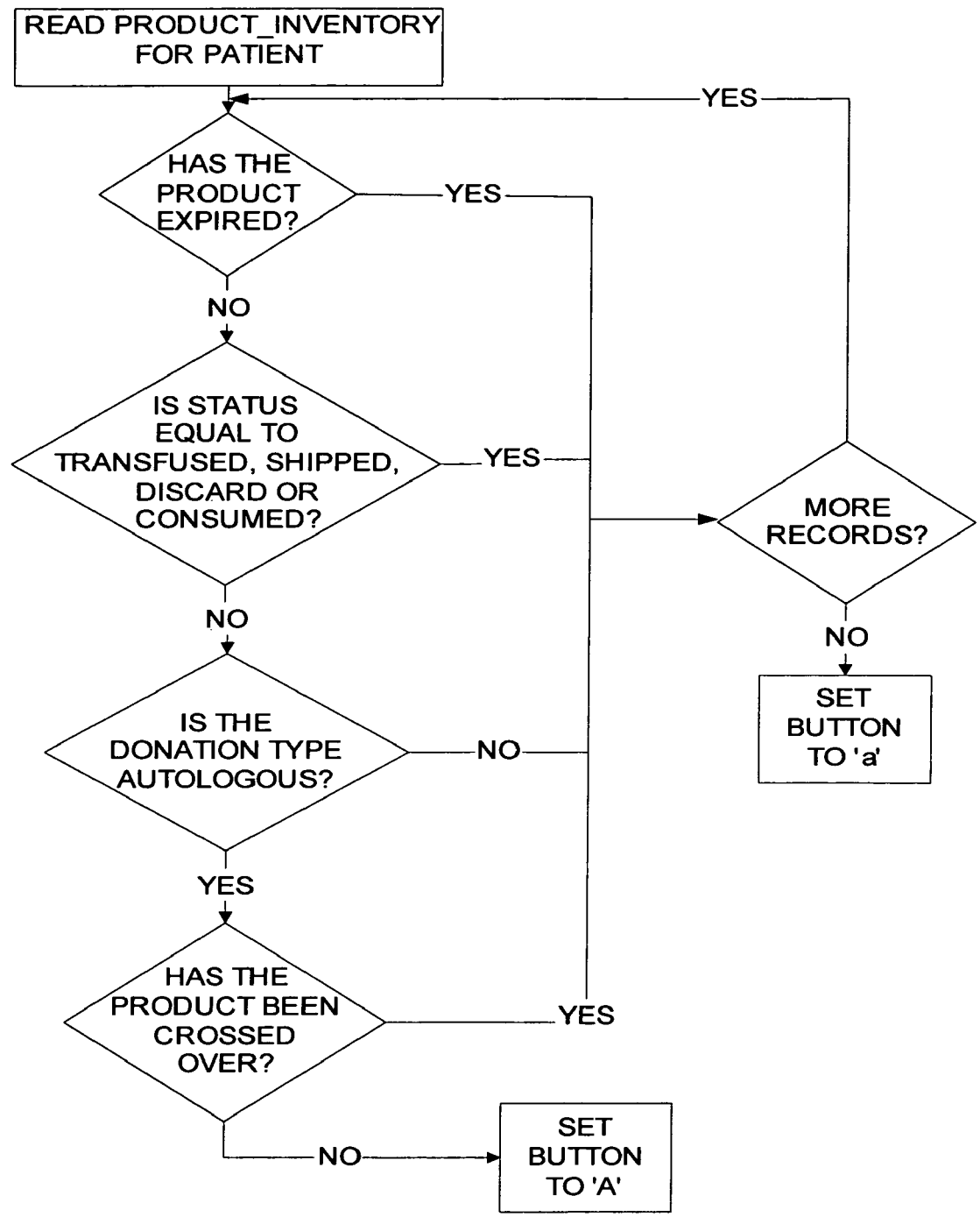
FIG. 12 is a flow chart of the logic used in button a of the patient bar.
Figure 13:
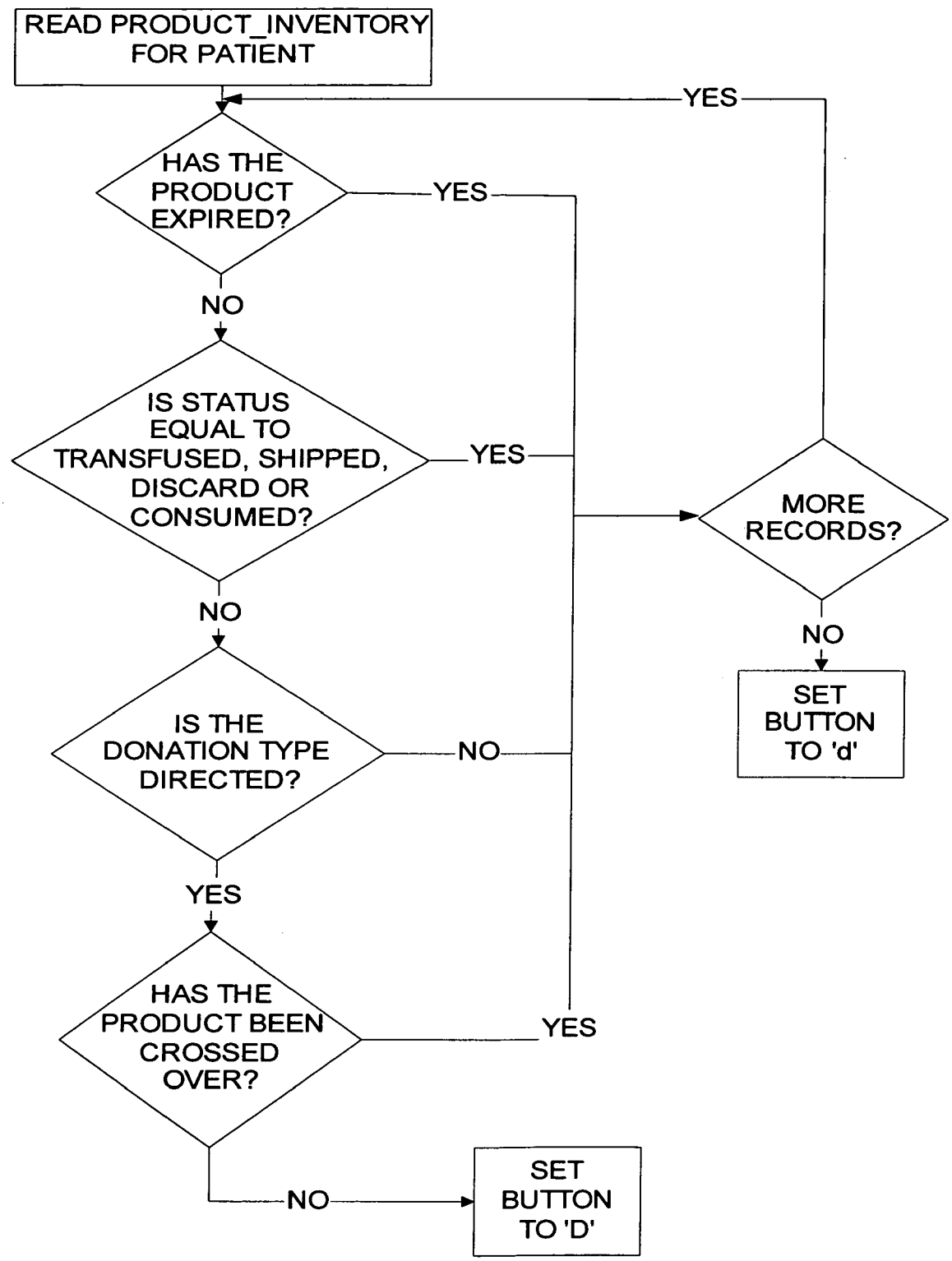
FIG. 13 is a flow chart of the logic used in button d of the patient bar.

The button d is a visual indication of a directed donation for the patient, not expired, not transfused, not shipped, not discarded, not consumed or crossed-over. If the button displays an uppercase "D", there is at least one such donation in inventory; otherwise, a lower case "d" means "none", as illustrated in FIG. 12.

Directed components are blood products (i.e. whole blood) which a donor has specifically designated for a particular patient's use. A patient who is scheduled for surgery where a transfusion may be required may have relatives or friends donate compatible blood specifically for use by a patient. This blood is categorized as directed and if deemed compatible is often preferred over other blood products available in the general inventory.

Significant antibodies indicate that the patient has had prior blood testing which has indicated the presence of unexpected or clinically significant antibodies, clinically significant antibodies being user-defined. The presence of these antibodies should be considered prior to issuing blood products for patient transfusion. The patient's blood attributes may constrain the blood products which are appropriate for use by the patient and/or require additional testing or modifications of blood products prior to transfusion.

Figure 14:
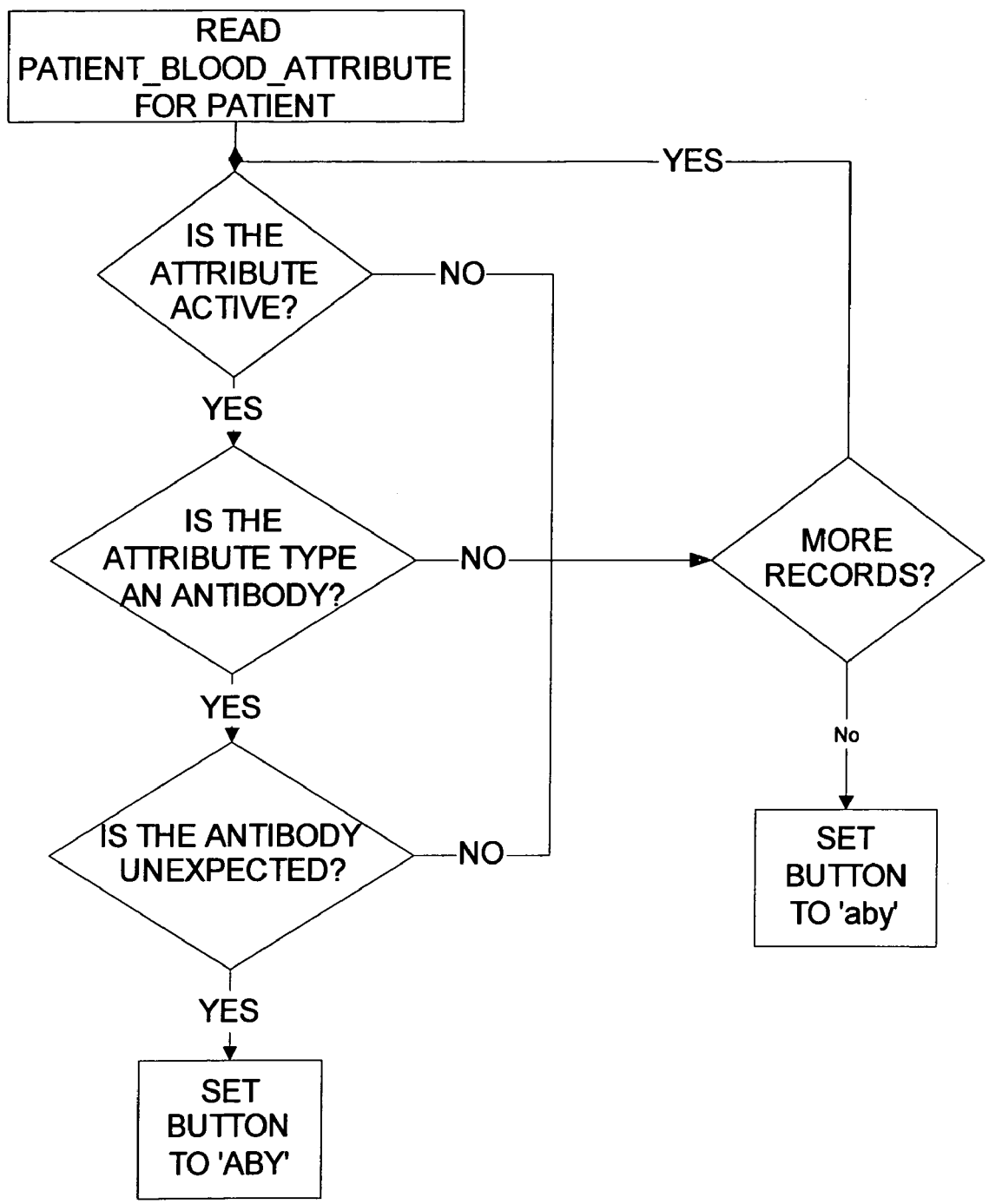
FIG. 14 is a flow chart of the logic used in button aby of the patient bar.

The button aby is an indication of whether the patient has unexpected antibody information. Referring to FIG. 14, if the button displays as upper case "ABY", there is information regarding unexpected antibodies; otherwise, lower case "aby" means "none" as illustrated in FIG. 14.

The next button presents the blood type of the patient, such as, "O Pos". This requires that the patient's blood type has been previously tested or was entered into the patient record. The blood type text contains the ABO and Rh components. The text for this is user modifiable but is generally standardized for ABO values, of "A,B,AB,O" and Rh values "POS" and "NEG". Therefore an example of a blood type caption presented might be "A POS". if the patient's blood type is unknown, the caption is left blank. Clicking on the blood type button accesses that information stored in the computer.

Figure 15:
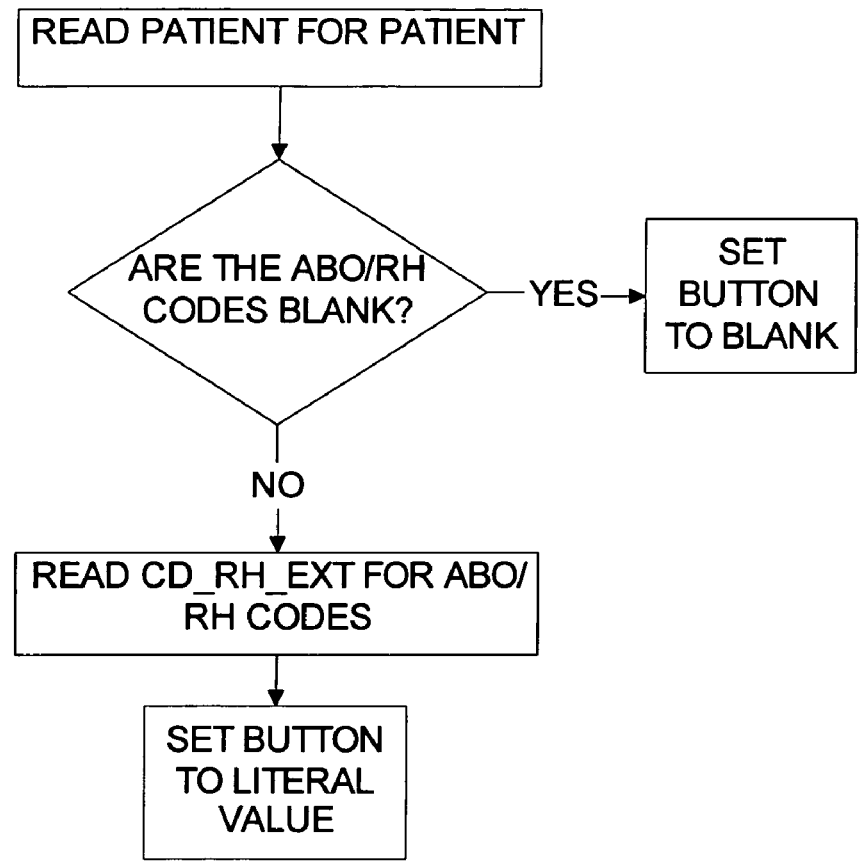
FIG. 15 is a flow chart of the logic used in conjunction with blood-type button "o-pos" of the patient bar.
Figure 16:
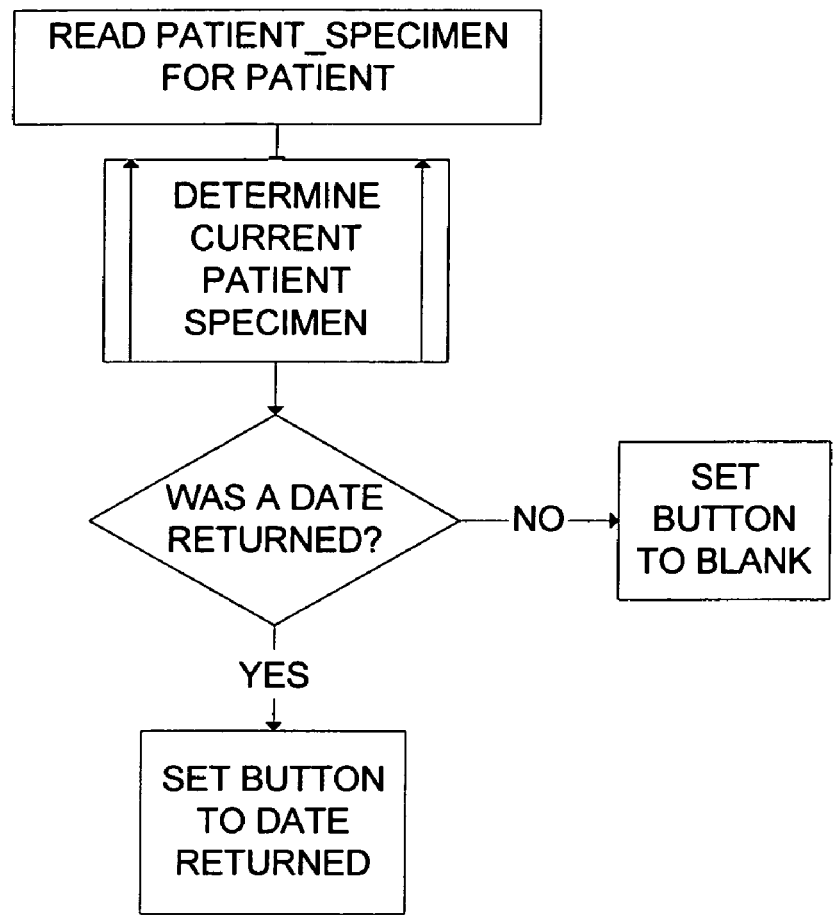
FIG. 16 is a flow chart of the logic used in conjunction with the specimen expiration date button of the patient bar.

The next button displays a patient's specimen expiration date. If there is a specimen that is current, active and available, then its expiration date displays as illustrated in FIG. 15. If no current active specimen is recorded for the patient or the specimen does not have an available status, no data is displayed on this button. Clicking on the button accesses the patient's specimen information stored in the computer.

Figure 17:
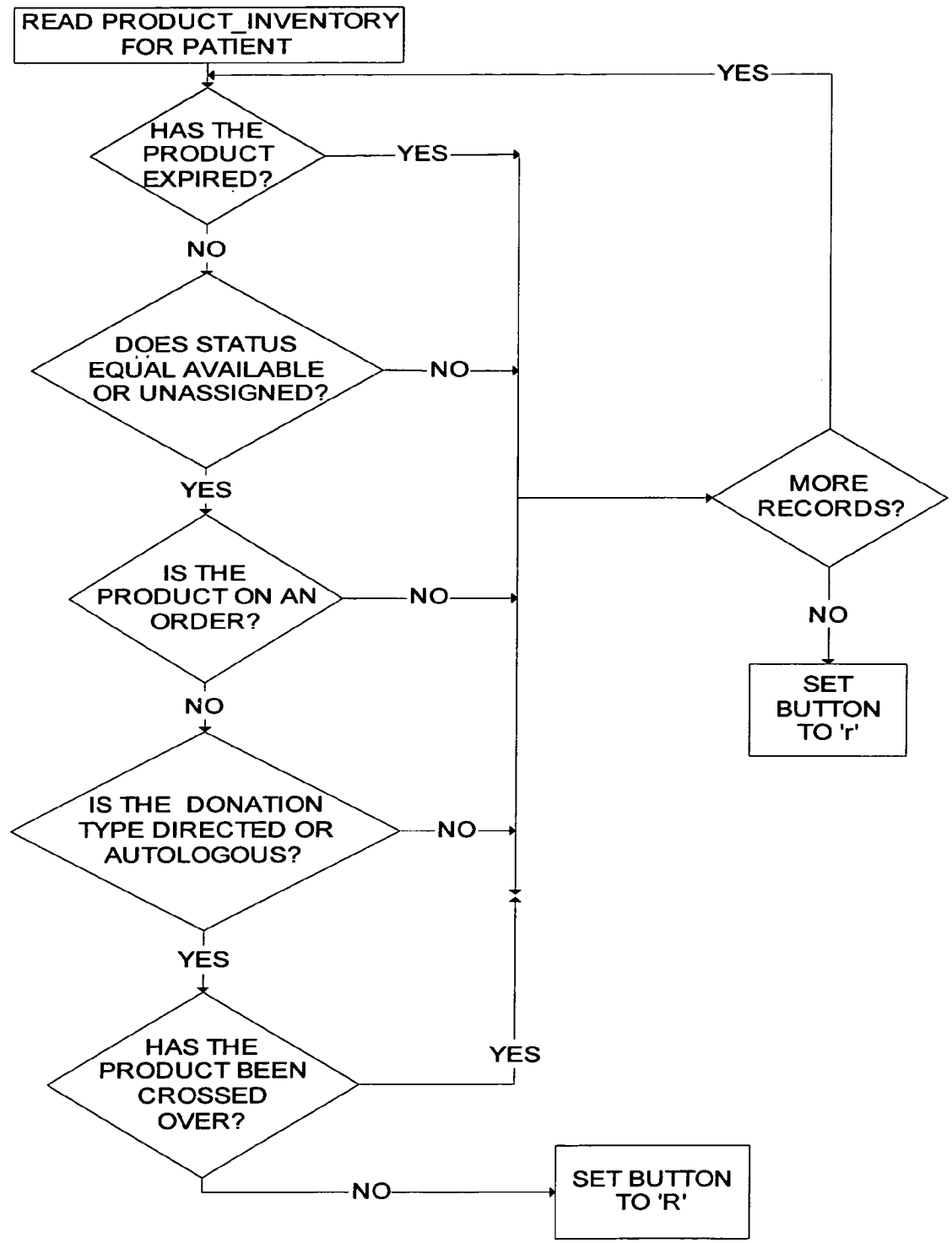
FIG. 17 is a flow chart of the logic used in conjunction with button r of the patient bar.

Reserved components are blood products which have been specifically linked for a particular patient's use. The last button "r" indicates whether reserved components are available for the patient. If the button displays as uppercase "R", then there is at least one such component in inventory; otherwise, "r" means none, as illustrated in FIG. 17.

Figure 21:
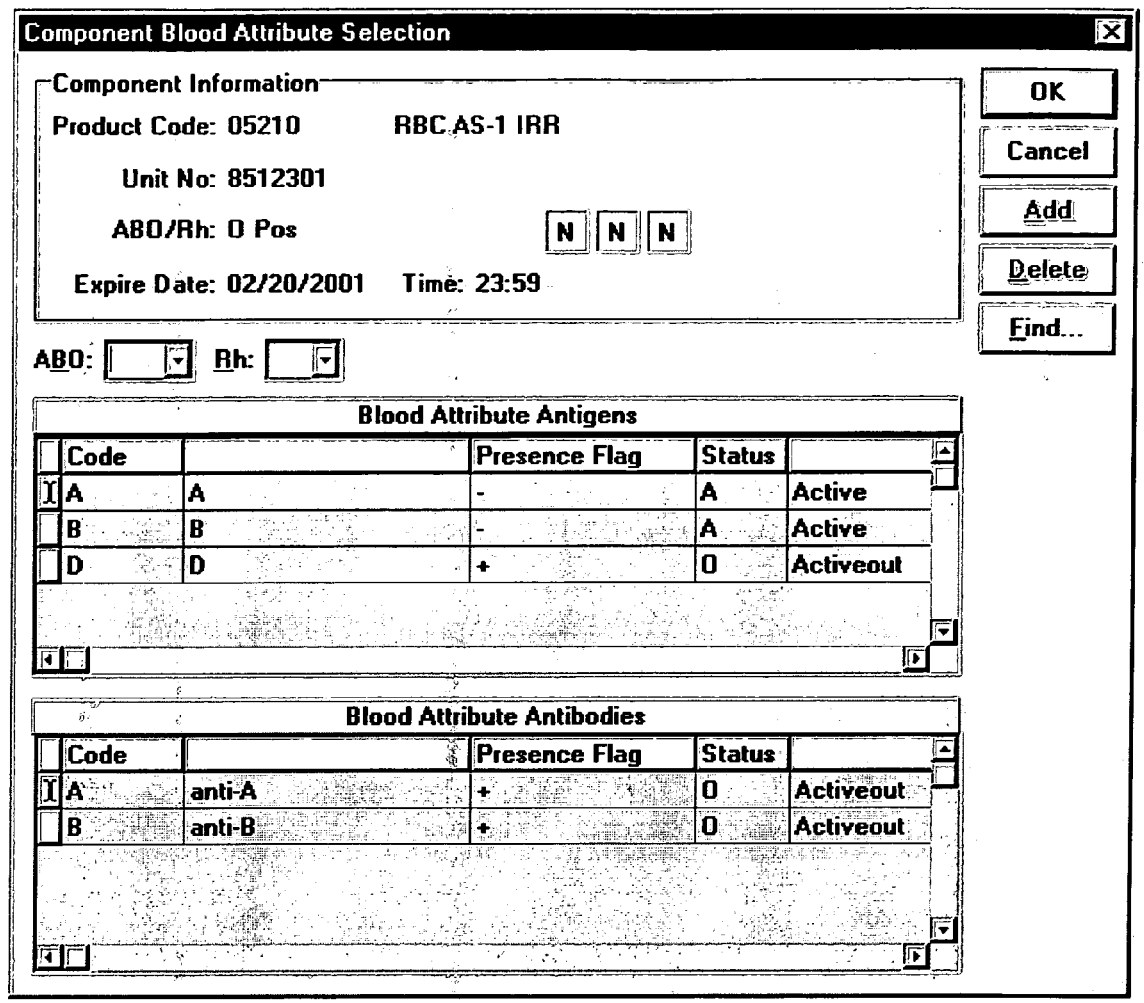
FIG. 21 is a screen display of component blood attribute information.

In practice, information relating to patient, blood products, component attributes may be recorded or stored in the database in the manner illustrated in FIGS. 20 to 22. As previously noted, FIG. 20 is a screen display of patient information including the patient bar P, FIG. 21 is a screen display of component blood attributes, and FIG. 22 illustrates information stored in tracking the location of blood components.

As soon as a blood component is received, it is assigned to a location within the central test facility. Throughout the life span of the blood component, the location of the component must be recorded, as illustrated in FIG. 22, before it can be transferred to another part of the facility or shipped outside the facility. If it is necessary to process the blood component, the computer verifies that the blood component is at the correct location for the work to be performed. Patient specimens and blood component segments are managed in a similar manner. Whenever a patient specimen or component segment is entered in the computer, it must be assigned to a location within the facility. The specimen or segment can only be used in processing if it resides at that location. If the specimen is needed by another facility, the transfer must be recorded in the computer system before it can be used by the receiving facility.

From the foregoing, FIGS. 1, 2 and 3 are intended to illustrate what is meant by "remote cross-matching" in which the cross-matching of each blood product and patient specimen is done at a facility remote from the patient. This avoids the necessity of maintaining a staff at each hospital but can only be done by maintaining records in the computer of the identity and location of the blood products and specimens.

FIGS. 4A and 15 is intended more to show the logic for determining compatibility of a given blood product and specimen based on blood attributes as illustrated in FIGS. 5 and 6. Strictly speaking, this is not cross-matching but can be used as a preliminary step for cross-matching. Thus, the system is capable of verifying the updates of blood attributes of the patient as well as blood products to assure that they are compatible as more information becomes available. In conjunction with physical cross-matching, blood attribute determination is helpful in ascertaining the compatibility of a given blood product and specimen.

FIGS. 7A and 7B is intended more to show the alternative of emergency supply of blood where there is no time to cross-match or identify the patient and is intended more as a means of assuring that the blood made available can be used with virtually any patient.

It is therefore to be understood that while one embodiment is herein set forth and disclosed, other modifications and changes may be made therein as defined by the appended claims and reasonable equivalents thereof.

We claim:

1. A method of managing and tracking blood products between a plurality of remote patient facilities and a central blood testing facility wherein a computer database is provided for storing information and wherein a blood specimen is obtained from each patient who requires a blood reserve for possible transfusion and said blood specimen is transferred to said central blood testing facility comprising the steps of:

providing an inventory of blood products at said central blood testing facility;

selecting one of said blood products which has an available segment at said central blood testing facility;

detaching said segment from said one of said blood products at said central blood testing facility;

transferring said one of said blood products from said central blood testing facility to one of said remote patient facilities at which said patient is located;

assigning said detached segment to said transferred blood specimen for cross-matching at said central blood testing facility;

determining the antigens and antibodies present in said one of said blood products and said transferred blood specimen;

remote serological cross-matching said transferred blood specimen and said detached segment at said central blood testing facility to determine their compatibility with one another, and entering the results in said database;

verifying the compatibility of said one of said blood products and said transferred blood specimen from the results entered in said database by comparing the antigens and antibodies in said detached segment and said transferred blood specimen to determine whether each is present in said detached segment and said transferred blood specimen tested, and storing compatibility results in said database thereof;

managing said blood products by preparing patient identification information relating to each of said blood products, each said detached segment and each said transferred blood specimen tested, and storing said information in said database at each of said central blood testing and remote patient facilities; and tracking the location and movement of each of said blood products, detached segments and transferred patient specimens between said remote patient facilities and said central blood testing facility by displaying the information stored in said database relating to their location and movement.

2. The method according to claim 1 including storing additional patient identification information relating to each patient's special needs, prior transfusion reaction history, autologous blood availability, directed blood components, blood type and patient specimen expiration date in said database.

3. The method according to claim 2 including the step of displaying said patient identification information on a computer at each of said remote patient facilities and central blood testing facility.

4. The method according to claim 3 including the step of displaying said patient information on a patient bar on each said computer which is accessible to all users regardless of their location at each of said facilities.

5. The method according to claim 2 including the step of selectively displaying the absence or presence of each item of information stored including special needs, patient comments, prior transfusion reaction history, autologous blood, availability, directed blood components blood type, presence of unexpected antibodies, patient specimen expiration date and reserved blood components.

6. The method according to claim 1 including the step of assigning each of said blood products and said transferred patient specimens to a location within each of said remote patient facilities and said central blood testing facility and tracking any movement of said blood products and said patient specimens to other locations.

7. The method according to claim 1 further characterized by cross-matching said detached segment and said transferred blood specimen at said central blood testing facility, assigning said detached segment and said transferred blood specimen to a location in said central blood testing facility and remote patient facility, and recording said location in said database.

8. The method according to claim 1 wherein the step of cross-matching includes the step of producing a product identification tag and attaching to each said one of said blood products tested.

9. A method for managing and tracking blood products patient specimens and segments between a plurality of hospitals and a central blood testing facility wherein a computer database is provided for recording information and a screen is provided for displaying said information, the method comprising the steps of:

obtaining a blood specimen from each patient requiring a blood product to be reserved for possible transfusion;

assigning a segment of a blood product for cross-matching;

remote serological cross-matching each said segment and said blood specimen at said facility to determine their compatibility with one another and entering results in said database;

managing each said segment and said patient specimen cross-matched by identifying each said segment, said component and said patient specimen with patient identification information and recording said patient identification information in said database; and tracking the location and movement of each of said segments, said products and said patient specimens between said hospitals and said facility.

10. A method according to claim 9 further characterized by verifying the presence of antigens and antibodies in each said segment and said patient specimen tested.

11. A method according to claim 10 including the step of determining said antigens and antibodies present in each said segment and said patient specimen prior to said cross-matching.

12. A method according to claim 11 characterized by periodically updating the compatibility of said antigens and antibodies and recording compatibility results of said antigens and antibodies in said database.

13. A method according to claim 9 including the step of tracking the location of each said segment and said patient specimen by recording their movement between said test facility and patient location.

14. A method according to claim 9 including the step of recording the antigens and antibodies present in each said patient specimen in said database.

15. A method according to claim 9 including the step of recording prior transfusion reaction history of each said patient in said database.

16. A method according to claim 9 including the step of recording autologous blood availability in said database.

17. A method according to claim 9 including the step of recording blood type of each said blood product and said patient specimen.

18. A method according to claim 9 including the step of recording the specimen expiration date of each said segment and said patient specimen.

19. A system for managing blood products and tracking their movement between a central blood testing facility and a plurality of hospitals wherein a computer is provided for processing data including a screen for displaying information, said system comprising:
managing means having first means including a database for entering information pertaining to each patient requiring a blood reserve, second means for entering blood type information for a blood specimen from each said patient, third means for recording a blood type for a blood product assigned to each said patient, fourth means for recording on said database results of comparing antigens and antibodies of each said patient specimen with said blood product;
fifth means for recording on said database results of remote serological cross-matching of each said patient specimen and said blood product; and
tracking means for tracking the location and movement of each of said blood products and patient specimens between said blood test facility and said hospitals by displaying on said screen the information stored in said database relating to their location and movement.

20. The system according to claim 19 including means for recording special needs of each said patient on said database including means for indicating the presence of said special needs.

21. The system according to claim 19 including sixth means for recording prior transfusion reaction history of each said patient including means for indicating the presence of a prior transfusion reaction.

22. The system according to claim 19 including seventh means for recording autologous blood availability and its location for each said patient including means for indicating the presence of an autologous donation for said patient.

23. The system according to claim 19 including eighth means for recording directed blood donations for each said patient including means for indicating the presence of said directed blood donations.

24. The system according to claim 19 including ninth means for recording the expiration date of each said patient specimen on said database including means for indicating the expiration date of each said blood specimen which is current and non-expired.

25. The system according to claim 19 including tenth means for comparing antigens and antibodies of each said patient specimen and said blood product.

26. The system according to claim 19 including eleventh means for recording components of said blood products which have been reserved for said patient including means for indicating the presence of said reserved components in inventory.

27. In a blood management system for managing information relating to blood products between a central blood test facility and one or more remote patient facilities wherein a computer is provided for processing data, a database is provided for recording said information and a screen is provided for displaying said information recorded, the improvement comprising:
managing means including means for recording information identifying each patient requiring a blood reserve on said database, means for obtaining and recording a blood specimen from each said patient, means for assigning a segment of a blood product for cross-matching, means for remote serological cross-matching each said segment and said patient specimen at said blood test facility to determine their compatibility with one another, means for identifying each said segment and said patient specimen, and means for assigning said segment, said blood product and said patient specimen to a location in one of said blood test facility and said remote patient facilities.

28. A system according to claim 27 including means for entering antigens and antibodies present in said blood specimen and said segment in said database; and means for comparing said antigens and antibodies to determine their compatibility.

29. In a blood management system according to claim 27 including means for displaying information relating to the location of each of said segments and said patient specimens.

* * * * *